United States Patent
Dea

(10) Patent No.: US 11,598,241 B2
(45) Date of Patent: Mar. 7, 2023

(54) FLUID LEVEL WAKE-UP FUNCTIONALITY

(71) Applicant: Caterpillar Inc., Peoria, IL (US)

(72) Inventor: Kevin Lloyd Dea, Morton, IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 17/316,700

(22) Filed: May 10, 2021

(65) Prior Publication Data
US 2022/0356826 A1 Nov. 10, 2022

(51) Int. Cl.
| F01N 3/20 | (2006.01) |
| G01M 15/10 | (2006.01) |
| G01F 23/30 | (2006.01) |
| G01N 33/00 | (2006.01) |
| B60R 16/023 | (2006.01) |
| B01D 53/94 | (2006.01) |
| B60Q 9/00 | (2006.01) |

(52) U.S. Cl.
CPC ......... *F01N 3/208* (2013.01); *B01D 53/9431* (2013.01); *B60Q 9/00* (2013.01); *B60R 16/023* (2013.01); *G01F 23/30* (2013.01); *G01M 15/102* (2013.01); *G01N 33/0063* (2013.01); *F01N 2610/1406* (2013.01); *F01N 2900/1814* (2013.01)

(58) Field of Classification Search
CPC combination set(s) only.
See application file for complete search history.

(56) References Cited

U.S. PATENT DOCUMENTS

| 7,610,750 B2 | 11/2009 | Viola et al. | |
| 9,243,755 B2* | 1/2016 | Lawrence | F01N 3/2066 |
| 9,382,828 B2 | 7/2016 | Wei et al. | |
| 9,862,273 B2* | 1/2018 | Shimazu | G08B 5/36 |
| 9,957,864 B2 | 5/2018 | Johnson et al. | |
| 10,684,196 B2 | 6/2020 | Singh et al. | |
| 2015/0019108 A1* | 1/2015 | Hendrickson | G01F 23/296 701/102 |
| 2016/0222856 A1* | 8/2016 | Kato | F02D 41/042 |
| 2017/0044949 A1* | 2/2017 | Khaled | F01N 3/208 |
| 2018/0326838 A1* | 11/2018 | Wolf | F01N 3/208 |
| 2020/0032694 A1* | 1/2020 | Fell | F01N 3/206 |
| 2020/0040787 A1* | 2/2020 | Brandt | G01N 29/024 |

FOREIGN PATENT DOCUMENTS

KR 20160065544 A 6/2016

* cited by examiner

*Primary Examiner* — Binh Q Tran
(74) *Attorney, Agent, or Firm* — Lee & Hayes, P.C.

(57) ABSTRACT

A reduction device includes a housing defining an input chamber configured to receive exhaust from a power source, an output chamber, an exhaust channel configured to direct the exhaust from the input chamber to the output chamber, and a longitudinal axis. The reduction device also includes a treatment unit disposed in the exhaust channel and along the longitudinal axis. The treatment unit is configured to at least partly remove pollutant species from the exhaust. The reduction device also includes an attenuation component disposed in the housing and radially outward of the treatment unit. The attenuation component is fluidly connected to the exhaust channel, and is configured to attenuate a range of frequencies corresponding to operation of the power source. Additionally, the exhaust channel prohibits exhaust entering the input chamber from exiting the housing without passing through the treatment unit.

20 Claims, 6 Drawing Sheets

FLUID LEVEL WAKE-UP FUNCTIONALITY

TECHNICAL FIELD

The present disclosure relates to monitoring systems configured to maintain emission quality for internal combustion engines. More specifically, the present disclosure relates to exhaust treatment systems that include monitoring components that are configured to monitor the exhaust treatment systems during key-off timeframes.

BACKGROUND

Internal combustion engines, including diesel engines, gasoline engines, natural gas engines, gaseous fuel-powered engines, and other engines known in the art exhaust a complex mixture of air pollutants. These air pollutants are composed of gaseous compounds such as nitrogen oxides ($NO_x$), and solid particulate matter also known as soot. Due to increased awareness of the environment, exhaust emission standards have become more stringent, and the amount of $NO_x$ and soot emitted to the atmosphere by an engine may be regulated depending on the type of engine, size of engine, and/or class of engine.

In order to ensure compliance with the regulation of $NO_x$, some engine manufacturers employ strategies in which the exhaust gas is passed through a diesel particulate filter (DPF), an oxidation catalyst, or other aftertreatment devices in order to remove particulates and other pollutants carried by the exhaust. Additionally, or alternatively, a selective catalytic reduction (SCR) process can be employed in which a gaseous or liquid diesel exhaust fluid (DEF) is injected into the exhaust gas stream and is absorbed onto a substrate. The DEF reacts with $NO_x$ in the exhaust gas to form $H_2O$ and $N_2$.

Current regulations associated with the SCR systems require that the SCR systems are to include the capability to execute quality detection of the DEF concentration that is utilized by the SCR system. Additionally, the regulations require the quality detection of the DEF concentration to occur at every key switch event and every storage tank fill event, leading to an increased number of cycles and the associated deterioration of detection systems. Further, current monitoring systems are configured to monitor the DEF tank during operation of the associated SCR systems utilizing the DEF. Accordingly, current monitoring systems of DEF concentration are unable to consistently monitor the storage tank and expose the detection systems for the DEF concentration to unnecessary use and deterioration.

An example system for preventing the injection of non-urea fluid into a urea storage tank for an SCR system is described in Korean Patent No. 2016/0065544 (hereinafter referred to as the '544 reference). In general, the '544 reference describes a method and system for preventing non-urea injection into a urea storage tank based at least on the state of a vehicle determined by an electric control unit associated with the vehicle. Additionally, the '544 reference describes that the system can be configured to prevent the vehicle from activating when foreign fluid is introduced into the urea storage tank. However, although the system described in the '544 reference includes a component detection sensor, a flow level sensor, and other sensors adapted to detect the chemical components and flow level of material being injected into the urea tank, the system is not configured to monitor the level and other characteristics of the fluid within the tank itself. Further, due to the large number of unique parts included in the system of the '544 reference, use of this system may increase the overall cost and complexity of the SCR system and associated devices.

Examples of the present disclosure are directed toward overcoming one or more of the deficiencies noted above.

SUMMARY OF THE INVENTION

Examples of the present disclosure are directed to a system that includes a storage tank, a fluid level sensor, a controller, a power source, and a memory. The storage tank can be configured to store an amount of diesel exhaust fluid (DEF) and can be fluidly connected to a selective catalytic reduction (SCR) system. Additionally, the fluid level sensor can be configured to determine the amount of DEF within the storage tank, wherein the fluid level sensor can be further configured to transmit first information indicating a first amount of DEF within the storage tank at a first time and second information indicating a second amount of DEF within the storage tank at a second time. Further, the controller can be in communication with the fluid level sensor, wherein the controller can be configured to receive the first information and the second information, determine a difference between the first amount and the second amount based on the first information and the second information, and generate an indication that the difference exceeds a threshold value. The power source can be operably connected to a direct power circuit and a switched power circuit, wherein the direct power circuit can be configured to supply power from the power source to the controller and the fluid level sensor during a key-off state of the SCR system and the switched power circuit can be configured to supply power from the power source to the controller and the fluid level sensor during a key-on state of the SCR system.

Further examples of the present disclosure are directed to a method that includes determining, with a low power circuit, that a primary system associated with a storage tank has entered a key-off state. Additionally, the method can include causing, based at least in part on determining that the primary system has entered the key-off state, a fluid level sensor within the storage tank to determine a first fluid level of a fluid within the storage tank at a first time and a second fluid level of the fluid within the storage tank at a second time. The method can include determining, with the low power circuit, that a difference between the first fluid level and the second fluid level exceeds a threshold. Based at least in part on determining that the difference exceeds the threshold, the method can include transmitting, with the low power circuit and to a direct power circuit operably connected to a power source, a command causing the direct power circuit to provide power from the power source to a tank controller. More specifically, the tank controller can generate an indication upon receiving the power via the direct power circuit, the indication configured to cause verification of the fluid upon the primary system entering a key-on state. Further, the method can include causing, based at least in part on the indication, the direct power circuit to provide the power to a recording system configured to store the difference and the indication to perform the fluid quality check.

Still further examples of the present disclosure are directed to a system that includes one or more processors and a memory storing one or more instructions that are executable by the one or more processors to perform one or more operations. The one or more operations can include determining that a circuit switch has transitioned a primary system from a key-on state to a key-off state and providing, from a power source and via a direct power circuit, power to a fluid level sensor associated with a storage tank. In particular, the fluid level sensor can determine, upon receiving power from the power source, a first fluid level of fluid within the storage tank at a first time and a second fluid level of the fluid within the storage tank at a second time different from the first time. Additionally, the one or more operations can include determining a difference between the first fluid level and the second fluid level, determining that the difference exceeds a threshold value, and providing power to a recording system operably connected to the one or more processors. More specifically, the power can be provided from the power source and via the direct power circuit based at least in part on a determination that the difference exceeds the threshold value. Further the recording system can be configured to store an indication that the difference exceeds the threshold value.

DETAILED DESCRIPTION

Systems and techniques described below are directed to monitoring components for reduction devices that comprise a diesel exhaust fluid (DEF) storage tank in addition to catalysts, exhaust processing components, and other internal components. As will be described below, example monitoring components of the present disclosure are configured to maintain substantially consistent monitoring of the storage tank and/or the SCR system for a combustion engine or other power systems to which they are connected.

Figure 1:
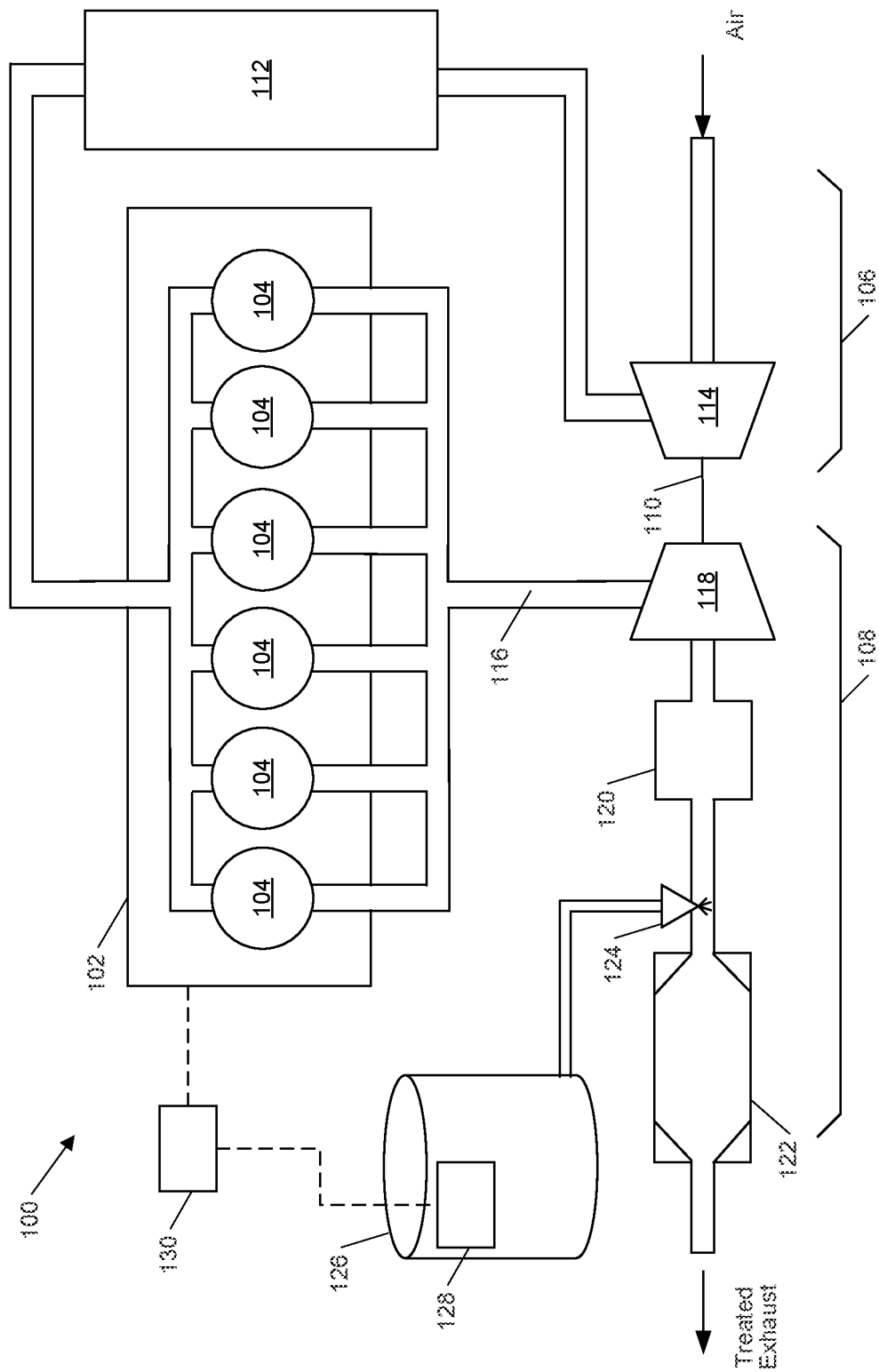
FIG. 1 illustrates an exemplary power system, such as a power system including a diesel-fueled internal combustion engine and a storage tank according to examples of the present disclosure.

FIG. 1 illustrates an exemplary power system 100. For the purposes of this disclosure, the power system 100 is depicted and described as a diesel-fueled, internal combustion engine. However, it is contemplated that the power system 100 may embody any other type of combustion engine, such as, for example, a gasoline, a hydrogen, a natural gas, a liquid fuel, or gaseous fuel powered engine. The power system 100 may include an engine block 102 having a plurality of cylinders 104, and a plurality of piston assemblies (not shown) disposed within the plurality of cylinders 104 to form combustion chambers. It is contemplated that the power system 100 may include any number of combustion chambers and that the combustion chambers may be disposed in an "in-line" configuration, a "V" configuration, or in any other conventional configuration. In at least one example, the diesel-fueled internal combustion engine can be a part of a set of generators (e.g., a "gen-set") that provide power for a facility. Accordingly, while the power system 100 is depicted as including a single engine block, the power system 100 can be configured to include a plurality of engine blocks. It should be noted that the power system can be any power generating component that utilizes an internal combustion engine such as the gen-set, a maritime engine, a motor, an industrial system that utilizes internal combustion, and other related applications.

Multiple separate sub-system may be included within the power system 100. For example, the power system 100 may include an air induction system 106 and an exhaust system 108. The air induction system 106 may be configured to direct air, oxidation agents, and/or an air and fuel mixture, into the power system 100 for subsequent combustion. The exhaust system 108 may exhaust byproducts of the combustion to the atmosphere.

The air induction system 106 may include multiple components that cooperate to condition and introduce compressed air into the plurality of cylinders 104. For example, the air induction system 106 may include an air cooler 112 located downstream of one or more compressors 114. The one or more compressors 114 may be connected to pressurize inlet air directed through the air cooler 112. It is contemplated that the air induction system 106 may include different or additional components than described above such as, for example, a throttle valve, variable valve actuators associated with each cylinder of the plurality of cylinders 104, filtering components, compressor bypass components, and other known components, if desired. It is further contemplated that the one or more compressors 114 and/or the air cooler 112 may be omitted, if a naturally aspirated engine is desired. In still further examples, the power system 100 of the present disclosure may include a recirculation loop (not shown) configured to direct a portion of the gases from the exhaust system 108 back into the air induction system 106 for subsequent combustion. It should be noted that the recirculation loop may be configured to extract exhaust from a location downstream of the one or more turbines 118 and direct the extracted exhaust to a location upstream of one or more compressors 114. Alternatively, the recirculation loop may be configured to extract exhaust from a location upstream of the one or more turbines 118 and direct the extracted exhaust to a location downstream of the one or more compressors 114).

The exhaust system 108 may include multiple components that condition and direct exhaust from the plurality of cylinders 104 to the atmosphere. For example, the exhaust system 108 may include an exhaust passageway 116, one or more turbines 118 driven by the exhaust flowing through the exhaust passageway 116, a particulate filter device 120 located downstream of the one or more turbines 118, a reduction device 122 fluidly connected downstream of the particulate filter device 120, and a DEF injection nozzle 124 located between the particulate filter device 120 and the reduction device 122. It is contemplated that the exhaust system 108 may include different or additional components than described above such as, for example, bypass components, an exhaust compression or restriction brake, an attenuation component, additional exhaust treatment devices, and other known components, if desired.

The one or more turbines 118 can be mechanically connected, via a drive shaft 110, to the one or more compressors 114. For example, rotation of the blades of the turbine 118 may drive commensurate rotation of the blades of the compressor 114 via the drive shaft 110. In some examples, the drive shaft 110 can also be connected to a drive system of a vehicle (not illustrated), a generator, or other system configured to drive rotation of the drive shaft 110 or that is driven by rotation of the drive shaft 110.

The particulate filter device 120 may comprise a particulate filter and is located downstream of the turbine 118 to remove particulates from the exhaust flow of the power system 100. The particulate filter device 120 may include an electrically conductive or non-conductive coarse mesh metal made from a metallic material or porous ceramic honeycomb medium made from a ceramic material. As the exhaust flows through the medium, particulates may be blocked by and left behind in the medium. Over time, the particulates may build up within the medium and, if unaccounted for, could negatively affect engine performance. To minimize negative effects on engine performance, the collected particulates may be passively and/or actively removed through a process called regeneration. When passively regenerated, the particulates deposited on the filtering medium may chemically react with a catalyst, for example, a base metal oxide, a molten salt, and/or a precious metal that is coated on or otherwise included within particulate filter to lower the ignition temperature of the particulates. The particulate filter device 120 may be closely located downstream of the engine block 102 (e.g., immediately downstream of the one or more turbines 118, in one example). A combination of passive and active regeneration may be utilized, if desired.

The reduction device 122 may receive exhaust from the one or more turbines 118 and reduce constituents of the exhaust to innocuous gases. In the example shown in FIG. 1, the reduction device 122 is disposed downstream of the particulate filter device 120 and the DEF injection nozzle 124. In other examples, the particulate filter device 120 may be omitted, and in such examples, a substrate, mesh, filtering medium, or other component of the reduction device 122 may perform the task of physically blocking and/or otherwise capturing particulates included in the exhaust. Similarly, the DEF injection nozzle 124 may be configured to inject DEF into an inner chamber of the reduction device 122. In any of the examples described herein, the reduction device 122 may embody a selective catalytic reduction (SCR) device that includes one or more treatment units comprised of a metal mesh, a ceramic honeycomb medium, and/or any other filtering medium coated with a reduction catalyst. In some examples, a gaseous or liquid diesel exhaust fluid (DEF) may be sprayed or otherwise advanced into the exhaust upstream of the one or more treatment units by the DEF injection nozzle 124. As the DEF is absorbed onto the surface of the one or more treatment units, the DEF may react with NOx (NO and $NO_2$) in the exhaust gas to form water ($H_2O$) and elemental nitrogen ($N_2$). In some embodiments, the catalytic compound(s) disposed on the one or more treatment units is configured to promote substantially even distribution and conversion of the pollutants and/or the DEF.

The DEF injection nozzle 124 may be configured to inject the DEF into the exhaust output from the one or more turbines 118 and/or the reduction device 122 to enable reduction of pollutants in the exhaust to innocuous gases. Additionally, the DEF injection nozzle 124 can be connected to a DEF storage tank 126 that stores the DEF for treatment of the exhaust. Further, the DEF injection nozzle 124 can be configured to provide the DEF to the exhaust at a rate determined to reduce the pollutants within the exhaust via the reduction device 122. Accordingly, the DEF injection nozzle 124 can be configured to receive the DEF from the DEF storage tank 126 and provide the reductant utilized by the reduction device 122 to convert pollutants to innocuous gases.

In some examples, the power system 100 may include a tank controller 128 associated with the DEF storage tank 126 and configured to ensure that the DEF stored by the DEF storage tank 126 satisfies a quality threshold (e.g., a DEF concentration threshold, a DEF composition threshold, etc.). In particular, the DEF provided to the DEF storage tank 126 can satisfy the quality threshold that provides a minimum DEF concentration for the DEF in the DEF storage tank 126. Additionally, the tank controller 128 can be configured to ensure that the DEF within the DEF storage tank 126 is not diluted, replaced, and/or other tampered with via a system of fluid level sensors, DEF sensors, electronic controls, and other sensors. The DEF sensors can be a set of sensors configured to detect the DEF concentration of the fluid within the tank. The fluid level sensors can be configured to detect when the fluid level within the DEF storage tank 126 experiences a change greater than a fluid level change threshold. The electronic controls can be a program configured to trigger the DEF sensors to evaluate the DEF within the DEF storage tank 126 in response to a detected condition.

In some examples, the tank controller 128 can be configured as a monitoring device for the DEF stored by the DEF storage tank 126. Additionally, the tank controller 128 can be an electronic control module (ECM) that is associated with the DEF storage tank 126. Alternatively, or in addition, the tank controller 128 can be in communication with a primary systems controller 130 that is configured to control operations of the engine block 102, the one or more compressors 114, the one or more turbines 118, and other components of the power system 100. In particular, the tank controller 128 can be configured to track system variables (e.g., temperature, pressure, fill level, etc.), triggers the provision of DEF to the DEF injection nozzle 124, and communicates with other controllers of the power system 100. Accordingly, the tank controller 128 can monitor the DEF storage tank 126 during standard operation of the power system 100 (e.g., while the power system 100 is in the key-on state) and maintain a low power monitoring state while the power system 100 is inactive (e.g., while the power system 100 is in the key-off state). Further, the tank controller 128 can include components that are selectively activated and deactivated based at least on the state of the power system 100, the DEF within the DEF storage tank 126, and other variables associated with the DEF storage tank 126.

In some examples, the electronic controls can be configured to trigger the DEF sensors to evaluate the DEF within the DEF storage tank 126 in response to a detected condition. More specifically, the detected condition that triggers the DEF sensors to evaluate the DEF within the DEF storage tank 126 can be at least one of a key-on event (e.g., an activation switch is turned on, an ignition is started, or other activation of the power system 100), a key-off event (e.g., an activation switch is turned off, an engine is shut down, or other deactivation of the power system), a DEF level change (e.g., the DEF storage tank 126 is filled with DEF, is emptied of DEF, or the DEF level within the DEF storage tank 126 is otherwise adjusted), a scheduled evaluation (e.g., the tank controller 128 is provided a monitoring schedule of DEF concentration evaluations that are to be completed over a period of time), and/or other detected condition. Additionally, the DEF sensors can be associated with an evaluation cooldown that prevents a series of evaluations to be rapidly triggered. For example, if a change in DEF level triggers a DEF concentration a minute before a scheduled DEF concentration evaluation, the scheduled DEF concentration evaluation can be delayed, rescheduled, canceled, and/or otherwise not provided based at least on the scheduled DEF concentration evaluation being within the evaluation cooldown triggered by the DEF concentration evaluation associated with the change in DEF level. Further, the DEF sensors can record the DEF concentration within the DEF storage tank 126 determined via the DEF concentration evaluation. Accordingly, a record of DEF concentration can be generated and detecting the DEF concentration to be below the quality threshold can trigger a maintenance request and/or notification to be transmitted to an administrator or other maintenance system that requests the DEF concentration be serviced and brought above the quality threshold and/or report the DEF concentration detected below the quality threshold.

Accordingly, the DEF storage tank 126 can be associated with a direct power circuit that enables the tank controller 128 to operate in a low power mode and determine whether the fluid within the DEF storage tank 126 has been tampered with and/or modified while the reduction device 122 is inactive. Further, the tank controller 128 can be configured to monitor the fluid level within the DEF storage tank 126 and record abnormal fluctuations in fluid level that are determined to indicate the stored fluid has been modified. The abnormal fluctuations can cause the tank controller 128 to trigger verification of the fluid within the DEF storage tank 126 upon activation of the reduction device 122 to ensure that diluted DEF is not injected into the reduction device 122, potentially damaging or degrading the catalysts within the reduction device 122, and/or reducing the efficacy of the reduction device 122 below industry standards.

In some examples, the primary systems controller 130 can be associated with the engine block 102, the one or more compressors 114, the one or more turbines 118, and/or other components of the power system 100. In particular, the primary systems controller 130 can be configured to monitor and control primary operations of the power system 100 while the power system 100 is operable and/or active. Additionally, the primary systems controller 130 can be configured to report the state of the power system 100 to the tank controller 128, request an amount of the fluid be provided from the DEF storage tank 126 via the DEF injection nozzle 124, and exchange communications with the tank controller 128. Further, the primary systems controller 130 can be configured to report the transitions of the power system 100 between an active state (e.g., a key-on state) and an inactive state (e.g., a key-off state). Accordingly, the primary systems controller 130 can transmit indications of the key-on state and/or the key-off state to the tank controller 128.

Figure 2:
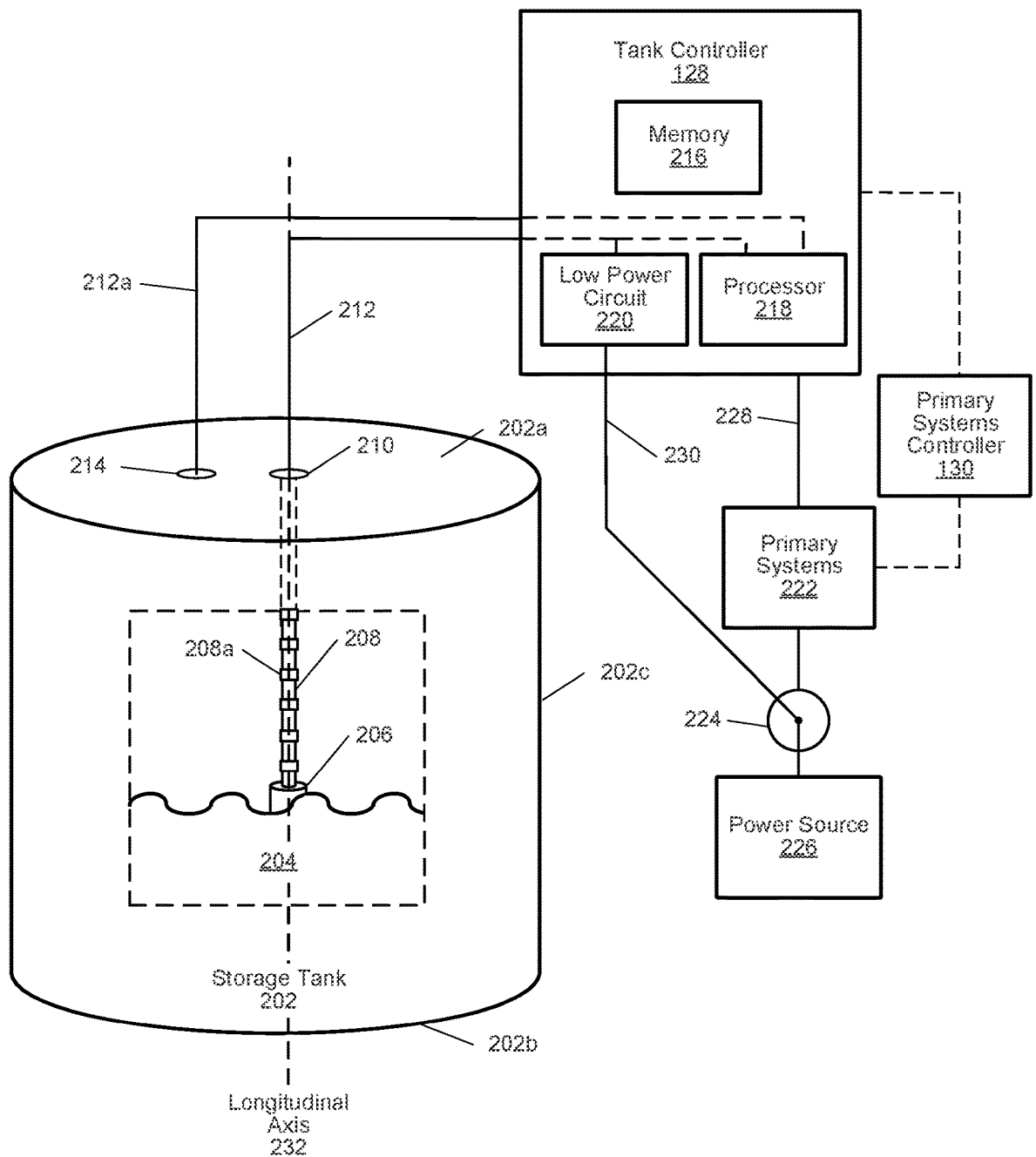
FIG. 2 is an illustration of a storage tank controller that is configured to monitor the storage tank during key-on and key-off system states.

FIG. 2 illustrates a monitoring system 200 for a storage tank. For the purposes of this disclosure, the monitoring system 200 is depicted and described as a monitoring system 200 for a storage tank 202 that holds liquid DEF in association with an SCR system (e.g., the reduction device 122) for treating exhaust from a diesel-fueled, internal combustion engine. However, it is contemplated that the monitoring system 200 may be configured to monitor storage tanks for additional fluids that undergo fluid quality checks for fluid composition and/or determining a quality for the stored fluid, such as whether the fluid satisfies composition guidelines, concentration guidelines, and other physical variables associated with the stored fluid. In any of the examples described herein, the storage tank 202 may be substantially similar to and/or the same as the DEF storage tank 126 described above with respect to FIG. 1.

In some examples, the storage tank 202 can comprise a first wall 202*a* and a second wall 202*b* that is substantially parallel to the first wall. More specifically, the first wall 202*a* can be a top of the storage tank 202 or a lid of the storage tank 202 that is opposite the second wall 202*b*, wherein the second wall 202*b* is a base of the storage tank. Additionally, a longitudinal axis 232 can extend substantially centrally through the storage tank 202 and substantially perpendicular to the first wall 202*a* and the second wall 202*b*. Alternatively, or in addition, the longitudinal axis 232 can be configured to extend substantially parallel to the direction of gravity and/or the direction in which the liquid DEF 204 rises and falls within the tank. It should be noted that in some additional examples, the first wall 202*a* and/or the second wall 202*b* may not be parallel to each other and/or perpendicular to the longitudinal axis 232 (e.g., the storage tank is not symmetrical and/or is not a regular shape). Further, a third wall 202*c* may be configured to connect the first wall 202*a* and the second wall 202*b*. The third wall 202*c* can be a sidewall that extends from the first wall 202*a* (e.g., from a lid of the storage tank 202) to the second wall 202*b* (e.g., to a base of the storage tank 202). Accordingly, the storage tank 202 can comprise an enclosed volume defined by the first wall 202*a*, the second wall 202*b*, the third wall 202*c*, and/or any additional walls of the storage tank 202 (e.g., the storage tank 202 can be substantially cylindrical, cuboid, etc.). The first wall 202*a*, the second wall 202*b*, the third wall 202*c*, and any additional walls of the storage tank 202 can be connected, as shown in the configuration shown in FIG. 2, via weld joints, secured via fasteners (e.g., screws, bolts, rivets, etc.), and/or be cast to form the storage tank 202. While FIG. 2 depicts the storage tank 202 as a cylinder having a substantially circular cross-section, the storage tank can take the form of a cylindrical prism, a cuboid, a triangular prism, a hexagonal prism, and/or other three-dimensional (3D) shapes for storage of the liquid DEF 204 (or other fluids).

In some examples, the storage tank 202 can contain the liquid DEF 204 and include a fluid level sensor 206. The fluid level sensor 206 can be attached to a sensor support 208 and output a signal via a sensor interface 210. The sensor support 208 can include one or more fluid level triggers 208*a* that enable the fluid level sensor 206 to determine the fluid level within the storage tank 202. In particular, the fluid level sensor 206 can be configured to locate a surface of the liquid DEF 204 within the storage tank 202 and determine a fluid level within the storage tank 202 that is associated with the surface of the liquid DEF 204. Additionally, the fluid level sensor 206 can be configured to determine the fluid level associated with the surface of the liquid DEF 204 based at least on a detected fluid level trigger 208*a*. As the fluid level within the storage tank 202 rises and falls, the fluid level sensor 206 can be configured to rise and fall along the sensor support 208 and pass one or more of the fluid level triggers 208*a*. Further, the fluid level sensor 206 can be configured to repeatedly determine the fluid level within the storage tank 202. For example, and at least at a first time and a second time, the fluid level sensor 206 can be configured to report a first fluid level for the first time and a second fluid level for the second time. Additionally, the fluid level sensor 206 can determine the first fluid level and the second fluid level based at least on the fluid level triggers 208*a*. Further, the fluid level sensor 206 can output the signal associated with the first fluid level and the second fluid level via the sensor interface 210. Accordingly, a tank controller 128 can receive the signal output by the fluid level sensor 206 via the sensor interface 210.

In some examples, the sensor support 208 can be configured to extend substantially parallel to the longitudinal axis 232. In particular, the sensor support 208 can extend from the sensor interface 210 (e.g., from a sensor interface 210 affixed to the first wall 202a) to a wall of the storage tank 202 (e.g., to the second wall 202b) Additionally, the sensor support 208 can enable the rise and fall of the fluid level sensor 206 with the surface of the liquid DEF 204. The fluid level sensor 206 can be at least partially affixed to the sensor support 208 such that the fluid level sensor 206 moves along the sensor support 208, wherein the fluid level sensor 206 can be loosely affixed to the support sensor so that such movement is possible (e.g., fluid level sensor 206 is mounted to a track on the sensor support 208 that it moves along). Further, the fluid level triggers 208a can be configured to determine the fluid level within the storage tank 202. In at least one example, the fluid level sensor 206 can be configured to determine the fluid level trigger 208a that it is currently in proximity of to determine an approximate height of the liquid DEF 204. The fluid level triggers 208a can be configured to indicate a percentage of the tank that the liquid DEF 204 occupies (e.g., a fluid level trigger 208a at 5%, 10%, 25%, 50%, 90%, etc.), a height of the liquid DEF 204 is from the second wall 202b of the storage tank 202 (e.g., a fluid level trigger at 1 inch, 2 inch, 6 inch, 18 inch, etc.), or other organizational system for identifying the fluid level within the storage tank 202.

In some additional examples, the sensor support 208 can be configured to provide an indication of fluid level within the storage tank 202. Alternatively, or in addition, the fluid level sensor 206 can be configured to provide the indication of fluid level within the storage tank 202. In particular, and independent of what provides the indication of fluid level, the fluid level sensor 206 and/or the sensor support 208 (optionally via the fluid level trigger(s) 208a) can be configured to output a voltage to the sensor interface 210 based at least in part on the fluid level within the storage tank 202. Alternatively, or in addition, the fluid level sensor 206 and/or the sensor support 208 (optionally via the fluid level trigger(s) 208a) can be associated with a microprocessor that is configured to generate an indication of fluid level based on the voltage output by the fluid level sensor 206 and/or the sensor support 208. Further, at least one of the indication of fluid level and/or the voltage output by the fluid level sensor 206 and/or the sensor support 208 can be transmitted to the tank controller 128 via the sensor interface 210. It should be noted that where the output of the fluid level sensor 206 and/or the sensor support 208 is a voltage, the sensor interface 210 can be configured to translate the voltage to the indication.

In some further examples, the storage tank 202 can include one or more additional sensors 214. For example, the storage tank 202 can include a thermocouple for detecting temperature within the storage tank 202, a DEF concentration sensor configured to determine whether the liquid DEF 204 satisfies a quality threshold, and/or other sensors related to a state of the liquid DEF 204 within the storage tank. Accordingly, an additional sensor(s) can be attached, affixed, and/or otherwise be mounted on/in the storage tank to generate additional data regarding the liquid DEF 204.

In some examples, a controller area network (CAN) 212 can be configured to connect the tank controller 128 to the fluid level sensor 206 and/or the one or more additional sensors 214. In particular, the CAN 212 can include a plurality of leads for transmitting power and signals between the fluid level sensor 206, the one or more additional sensors, and/or the tank controller 128. The fluid level sensor 206 and the one or more additional sensors can be connected via a single CAN 212 connection and/or via one or more additional CAN connections 212a. Accordingly, the CAN 212 can be configured to individual or in combination transmit the fluid level of the storage tank and/or one or more additional variables associated with the storage tank 202. Further, the CAN can be configured to power the fluid level sensor 206 and/or the one or more additional sensors 214.

In some examples, the tank controller 128 can include a processor 218 and a low power circuit 220 that are configured to receive an indication of state variables of the storage tank 202 such as fluid level, temperature, DEF concentration, and/or other indications from the fluid level sensor 206 and/or the one or more additional sensors 214 via the CAN 212 (and/or 212a). In particular, the processor 218 can be configured to receive the indication(s) via the CAN 212 in association with operation of primary systems 222. It should be noted that the primary systems 222 can include control systems associated with the power system 100, components of the power system (e.g., the engine block 102, a turbine 118, a compressor 114, a reduction device 122, etc.), a drive system (e.g., the monitoring system is mounted on a piece of construction equipment capable of movement), and other systems that are active during normal operation of the power system or other system that the monitoring system 200 is associated with. Additionally, the processor 218 can be configured to be active during normal operation of the tank controller 128 while the monitoring system 200 is in a key-on state. The key-on state can be associated with a state where the primary systems 222 have been turned-on and/or activated by a user and/or administrator associated with the primary systems. For instance, a circuit switch 224 can be associated with a first position (not illustrated) that corresponds to a key-on/activated state for the primary systems 222. Accordingly, the processor 218 can receive power from a power source 226 via the primary systems 222 and a switched power circuit 228.

The processor 218 and/or the low power circuit 220 of the tank controller 128 can be configured to receive sensor data that is indicative of fluid level, temperature, DEF concentration, and/or other indications from the fluid level sensor 206 and/or the one or more additional sensors 214 via the CAN 212 (and/or 212a). In particular, the low power circuit 220 can be configured to receive at least the indication of fluid level from the fluid level sensor 206 via the CAN 212 while the primary systems 222 are deactivated and/or in a key-off state. Additionally, the low power circuit 220 can be configured to receive power from the power source 226 via a direct power circuit 230. The direct power circuit 230 can be configured to draw sufficient power to activate the low power circuit 220, the fluid level sensor 206, and communication link to the CAN 212. Accordingly, the low power circuit 220 can be active during the key-off state of the primary systems 222 and receive power directly from the power source 226 to maintain operation of the fluid level sensor 206 while the primary systems 222 are in the key-off state. Further, the direct power circuit 230 can be configured to be always connected (not illustrated) or be connected when the system is in the key-off state as illustrated by FIG. 2.

It should be noted that the low power circuit 220 can be configured to monitor the storage tank 202 as a low power controller of the storage tank 202 and/or the fluid level sensor 206 during a key-off state of the primary systems 222. In particular, the low power circuit 220 can be configured as a low power logic circuit that may store first information associated with a first fluid level determined and provided by the fluid level sensor 206 at a first time and second information associated with a second fluid level determined and provided by the fluid level sensor 206 at a second time. Additionally, the low power circuit 220 may include sufficient computational power to determine a difference between the first fluid level and the second fluid level based on the first information and the second information. Alternatively, or in addition, the low power circuit may include a microprocessor or processor that is configured to determine the difference between the first fluid level and the second fluid level. Further, the low power circuit can be configured to determine whether the difference exceeds a threshold value and transmit, to the tank controller 128 or the processor 218, a wake-up signal that triggers additional responses to the difference determined by the low power circuit.

In some examples, a primary systems controller 130 that is associated with the primary systems 222 can be configured to report the state of the primary systems 222 and/or the state of the circuit switch 224 to the tank controller 128. In particular, the primary systems controller 130 controls primary operations of the primary systems 222 while the circuit switch 224 is in the key-on state and the primary systems 222 are operable and/or active. Additionally, the primary systems controller 130 can be configured to report the transitions of the circuit switch 224 from the key-on state to the key-off state and from the key-off state. Similarly, the primary systems controller 130 can be configured to report the active and/or inactive state of the primary systems 222. Accordingly, the primary systems controller 130 can transmit indications of the key-on state and/or the key-off state to the tank controller 128.

In some examples, the tank controller 128 can store current values of the state variables within the memory 216 and/or utilize the current values to determine whether maintenance is to be provided for the liquid DEF 204. In particular, the tank controller can determine whether maintenance is to be provided based on determinations made by the processor 218 (e.g., a cooling system is to be activated, a heater is to be activate, a refill for the liquid DEF is to be provided, etc.). Additionally, the tank controller 128 can be configured to cause the storage tank 202 to output the liquid DEF 204 to the primary systems 222. For example, the tank controller 128 can be in communication with the primary systems controller 130 associated with the primary systems 222 that transmits a request for an amount of the liquid DEF 204 via the DEF injection nozzle 124. The tank controller 128 can receive the request and control a valve (not illustrated) to open and/or a pump (not illustrated) to activate, exposing a fluid channel (e.g., a pipe, a conduit, etc.) to fluid communication with the storage tank 202 and transporting the liquid DEF 204 from the storage tank to the DEF injection nozzle 124 associated with the primary systems 222. Additionally, the tank controller 128 can further transmit commands to the fluid level sensor 206, the one or more additional sensors 214, the primary systems controller 130, one or more valves associated with the fluid channel and/or the DEF injection nozzle 124, and/or other components associated with the storage tank 202.

In some examples, the memory 216 can be volatile (such as RAM), non-volatile (such as ROM, flash memory, etc.) or some combination of the two. The memory 216 may include removable storage, non-removable storage, and other forms of computer-readable media including, but not limited to RAM, ROM, EEPROM, flash memory, other memory technologies, CD-ROM, DVDs, content-addressable memory (CAM), other optical storage, magnet storage, and any other medium which can be used to store indications of fluid level, fluid level difference, fluid verification requests, the DEF concentration check request, and other indications generated and provided by the low power circuit 220 and/or the processor 218. Additionally, the memory 216 can be configured to store a record of the fluid level that is generated in response to a wake-up signal transmitted by the low power circuit 220 based on a fluid level difference exceeding the threshold value. Accordingly, the memory 216 can be configured to store, in response to the wake-up signal, the record generated in response to a detected potential tampering event identified by the low power circuit 220 based on the fluid levels detected by the fluid level sensor 206. It should be noted that the memory 216 can comprise one or more instructions that are executed by the tank controller 128 and/or the processor 218 and cause the tank controller 128/the processors 218 to perform operations of the methods discussed below.

In some examples, processor(s) 218 can be configured to execute operations determined based on instructions stored in the memory 216. In particular, the processor 218 can be configured to receive sensor data from the fluid level sensor 206 (e.g., information that indicates a fluid level of the liquid DEF 204 within the storage tank 202), receive additional sensor data from the one or more additional sensors 214, transmit commands that cause the direct power circuit 230 to provide power from the power source 226 to individual components associated with the storage tank 202 during the key-off state of the primary systems 222, and other control functions associated with the storage tank 202 (e.g., transmit a command to a valve that connects the storage tank 202 with the fluid channel to the DEF injection nozzle 124). Additionally, the processor 218 can be configured to monitor the liquid DEF 204 within the storage tank 202 during the key-on state and the key-off state of the primary systems 222. Alternatively, or in addition, the processor 218 can be configured to receive a wake-up signal from the low power circuit and perform a series of operations in response to the wake-up signal. It should be noted that the processor 218 can be a central processing unit (CPU), a graphics processing units (GPU), both a CPU and a GPU, and/or other processing units or components known in the art.

In some examples, the power source 226 can include at least a battery and/or a power generator that can be configured to provide power to the tank controller 128, the processors 218, the low power circuit 220, and/or the primary systems 222 dependent at least on the state of the monitoring system 200 and/or the primary systems 222 (e.g., key-on state, key-off state, etc.). In particular, the power source can be configured to include at least a battery that provides power to the tank controller 128 and the processor 218, via the switched power circuit 228, during the key-on state. Similarly, the power source can be configured to include at least the battery configured to provide power to the low power circuit 220, via the direct power circuit 230, during the key-off state. The power source 226 can be configured to satisfy a controller power demand, one or more fluid sensor power demands, a primary system power demand, and/or other power demands via the switched power circuit 228 and/or the direct power circuit 230 based on the state of the primary systems 222.

In some examples, the low power circuit 220 can be configured to monitor the storage tank 202 during the key-off state for the primary systems 222. In particular, the low power circuit 220 can receive power from the power source 226 via the direct power circuit 230. Additionally, the low power circuit 220 can be configured to maintain a connection, via the CAN 212 with the fluid level sensor 206 and provide the fluid level sensor 206 power for determining the fluid level of the storage tank. Further, the low power circuit 220 can cause the fluid level sensor 206 to determine a current fluid level of the storage tank 202 via the CAN 212. For example, and while the primary systems 222 are in the key-off state, the low power circuit 220 can be associated with a monitoring schedule that is configured to cause the fluid level sensor 206 to determine a fluid level within the storage tank 202 at individual points in time. Additionally, the low power circuit 220 can cause power to be transmitted, via the CAN 212, to the fluid level sensor 206 to enable the fluid level to be determined. Further, the low power circuit 220 can receive the fluid level within the storage tank 202 from the fluid level sensor 206 and determine whether the fluid (e.g., the liquid DEF 204) within the storage tank 202 has been tampered with. Accordingly, the low power circuit 220 can be configured to monitor the liquid DEF 204, via the fluid level sensor 206, while the primary systems 222, the processor 218, and the tank controller 128 are partially and/or completely unpowered.

In some additional examples, the low power circuit 220 and the processor 218 can be configured to monitor the storage tank 202 during the key-off state for the primary systems 222. In particular, the low power circuit 220 and the processor 218 can receive power from the power source 226 via the direct power circuit 230. Additionally, and similar to the above example, the low power circuit 220 can be configured to maintain a connection, via the CAN 212 with the fluid level sensor 206 and provide the fluid level sensor 206 power for determining the fluid level of the storage tank. Further, the low power circuit 220 can cause the fluid level sensor 206 to determine a current fluid level of the storage tank 202 by sending an indication and/or a request for the current fluid level via the CAN 212. For example, and while the primary systems 222 are in the key-off state, the low power circuit 220 can be associated with a monitoring schedule that is configured to cause the fluid level sensor 206 to determine and report a fluid level within the storage tank 202 at individual points in time. Additionally, the low power circuit 220 can be configured to receive the fluid level from the fluid level sensor 206 and transmit the fluid level to the processor 218. Further, the processor 218 can be configured to determine, based at least on the fluid level, whether the fluid (e.g., the liquid DEF 204) within the storage tank 202 has been tampered with. Accordingly, the processor 218 and the low power circuit 220 can be configured to monitor the liquid DEF 204, via the fluid level sensor 206, while the primary systems 222 and the tank controller 128 are partially and/or completely unpowered.

In general, the tank controller 128 can be programmed to operate in a standard operation mode (e.g., the tank controller 128 and its components are powered via the switched power circuit) and a low power mode (e.g., components of the tank controller 128 are powered via the direct power circuit). In particular, the standard operation mode can be configured such that while the primary systems 222 are active and the system is in a key-on state, the tank controller 128 operates at full capacity regarding the maintenance of the fluid within the storage tank 202 (e.g., monitoring fluid levels for the liquid DEF 204, determining the DEF concentration, determining the DEF composition, monitoring system variables for the liquid DEF 204 and the storage tank 202, etc.). Similarly, the low power mode can be configured such that while the primary systems 222 are inactive and the system is in a key-off state, the tank controller 128 suspends normal operation and components of the tank controller 128, such as the low power circuit 220 and/or the processor 218, operate to monitor the storage tank 202. In at least one embodiment, the low power circuit 220 can include a microprocessor (or other processor) configured to receive an indication of the fluid level within the storage tank 202, via the CAN 212, from the fluid level sensor 206. Additionally, the low power circuit 220 can be configured to determine, based on the indication received from the fluid level sensor 206 whether the fluid within the storage tank 202 has been tampered with. Further, and in response to determining that the fluid has been tampered with, the low power circuit 220 can be configured to transmit a wake-up signal to at least one of the tank controller 128 and/or the processor 218 that triggers verification processes for the fluid within the storage tank. In at least one additional embodiment, the low power circuit 220 can be configured as an interface between the fluid level sensor 206 and the processor 218. In particular, the processor 218 can be configured to receive the indication of fluid level from the fluid level sensor 206 via the low power circuit 220. Additionally, the processor 218 can be configured to determine based on the indication received from the fluid level sensor 206 whether the fluid within the storage tank 202 has been tampered with. Further, the processor 218 can cause the tank controller 128 to perform verification processes for the fluid within the storage tank upon returning to the standard operation mode. It should be noted that the low power circuit 220 and/or the processor 218 can be configured to transmit a wake-up signal for the tank controller 128, additional wake-up signals for components of the tank controller 128, and/or cause the tank controller 128 to perform verification of the fluid within the storage tank 202 upon returning to the standard operation mode.

In some examples, the low power circuit 220 can be configured to monitor the storage tank 202 during the key-off state for the primary systems 222. In particular, the low power circuit 220 can be configured to obtain a baseline fluid level associated with the storage tank 202 and the liquid DEF 204 captured before or during a transition from a key-on state to the key-off state. Additionally, the low power circuit 220 can be configured to determine a monitoring schedule for collecting the fluid level from the storage tank 202. The low power circuit 220 can be configured to substantially continuously, periodically, aperiodically, and/or regularly (e.g., based on the monitoring schedule) determine a current fluid level associated with the storage tank 202 at a time. Further, the low power circuit 220 can be configured to determine, based on the fluid level and the current fluid level, a fluid level difference that indicates a change in fluid level between a first time associated with the key-on to key-off transition and/or a previous measurement of the fluid level via the fluid level sensor 206 and a second time associated with the low power circuit 220 determining the current fluid level. Accordingly, the low power circuit 220 can be configured to provide at least power to the fluid level sensor 206 and cause the fluid level sensor 206 to obtain the current fluid level at the second time for comparison against the fluid level at the first time.

In some examples, the low power circuit 220 can be configured to monitor the storage tank 202 during the key-off state for the primary systems 222. In particular, the low power circuit 220 can be configured to determine whether the fluid level difference exceeds a threshold value. The threshold value can represent a threshold fluid level difference that is indicative of potential tampering with the fluid within the storage tank 202 and/or abnormal events while the tank controller 128 and the primary systems 222 are in the key-off state. Alternatively, or in addition, the threshold value can represent a maximum allowable fluid level difference, wherein fluid level differences exceeding the threshold value are determined to indicate tampering with and/or modification of the fluid within the storage tank 202. The threshold fluid level difference can represent a threshold percentage change in the fluid level (e.g., a change in the fluid level exceeding 10% of the total volume of the storage tank 202), a threshold volume change within the storage tank 202 (e.g., the first fluid level is associated with 10 gallons of fluid within the storage tank 202, the second fluid level is associated with 15 gallons of fluid within the storage tank 202, and the threshold value is 5 gallons of fluid), and/or other variables associated with the fluid stored within the storage tank 202. Additionally, the threshold value can indicate a minimum fluid level change that has been associated with triggering a DEF concentration check and/or other verification processes for the liquid DEF 204 (or other fluid) within the storage tank 202. The DEF concentration check and/or other verification processes can be performed in response to the tank controller 128 transitioning from the low power mode to the standard operation mode (e.g., key-off state transitions to key-on state). For example, the low power circuit 220 can be configured to receive a first fluid level and a second fluid level from the fluid level sensor 206 (e.g., the first fluid level can be reported by the fluid level sensor 206 at a first time and the second fluid level can be reported by the fluid level sensor 206 at a second time) and determine the fluid level difference based on the first fluid level and the second fluid level. Additionally, the low power circuit 220 can be configured to determine, based at least on a threshold value that defines the minimum fluid level change, that a wake-up signal is to be transmitted to the processor 218 and/or the tank controller 128. Accordingly, the low power circuit 220 can compare the fluid level difference, determined based at least on the first fluid level and the second fluid level obtained from the fluid level sensor 206, and cause the DEF concentration check and/or other fluid verification processes to be performed upon the tank controller 128 returning to the standard operation mode. It should be noted that in some embodiments, the first fluid level can be a current fluid level within the storage tank 202 and the second fluid level can be a previous fluid level within the storage tank 202.

In at least one example, the low power circuit 220 can be configured to determine that the processor 218 of the tank controller 128 is to be activated based at least on the fluid level difference exceeding the threshold value. In particular, the low power circuit 220 can be configured to determine that a wake indication is to be transmitted to at least the processor 218 based at least on the fluid level difference exceeding the threshold value. Additionally, the wake indication can trigger the processor to generate an indication of the fluid level difference exceeding the threshold value, and capture the current state of the storage tank 202. It should be noted that the low power circuit 220 can be configured to transmit the indication, provide power to the processor 218, provide power to the fluid level sensor 206, and/or provide power to the one or more additional sensors 214 via the CAN 212 and/or the one or more additional CAN connections 212*a*. Accordingly, the wake indication can trigger the processor to activate, receive power from the low power circuit 220, and evaluate the liquid DEF 204 within the storage tank 202.

In at least one additional example, the low power circuit 220 can be configured to determine that the liquid DEF 204 is to be verified (e.g., DEF concentration determined) based at least on the fluid level difference exceeding the threshold value. In particular, the low power circuit 220 can be configured to determine that the fluid level difference (e.g., a change in fluid level from a first fluid level to a second fluid level) exceeds the threshold value (e.g., a threshold change in fluid level, a maximum allowable fluid level difference, etc.) and generate an indication that the fluid level difference exceeds the threshold value. The indication can be recorded and configured to cause the tank controller 128 to trigger verification of the liquid DEF 204 (or other fluid) within the storage tank 202. Additionally, the indication that the fluid level difference exceeds the threshold value can flag the liquid DEF 204 for a determination of DEF concentration within the storage tank 202. More specifically a record can be generated by the low power circuit 220 and/or the processor 218 during the key-off state that can cause the processor 218 and/or the tank controller 128 to trigger a DEF concentration check upon an additional transition from the key-off state to the key-on state. Further, the flag can include the current fluid level and/or the fluid level difference that triggered the flag to be generated for the DEF concentration check caused by tank controller 128 (and/or processor 218). Accordingly, the flag can be saved to a memory 216 associated with the tank controller 128 such that the tank controller 128, upon receiving power from the power source 226 via the switched power circuit 228, causes the tank controller 128 to trigger the DEF concentration check or causes an associated system (e.g., the processor 218) to trigger the DEF concentration check.

Accordingly, the direct power circuit 230 can be configured to power the tank controller 128 and/or components of the tank controller 128 such as the low power circuit 220 and/or the processor 218 to monitor the liquid DEF 204 (or other fluid within the storage tank 202) during a key-off state (deactivated) of the primary systems 222. The direct power circuit 230 can provide power for at least the fluid level sensor 206 and the low power circuit 220 such that fluctuations in fluid level within the storage tank 202 are identified by the low power circuit 220 (or the processor 218) based on fluid levels reported by the fluid level sensor 206. Further, where the low power circuit 220 (or the processor 218) determines that a fluid level difference exceeds a threshold value, a wake-up signal can be transmitted to the tank controller 128, the processor 218, and/or the memory 216 that causes a record to be generated. The record can trigger fluid verification (determining the DEF concentration and/or DEF composition) upon the primary systems 222 resuming activity (e.g., transition from key-off state to key-on state) to ensure that the liquid DEF 204 satisfies one or more quality thresholds.

Figure 3:
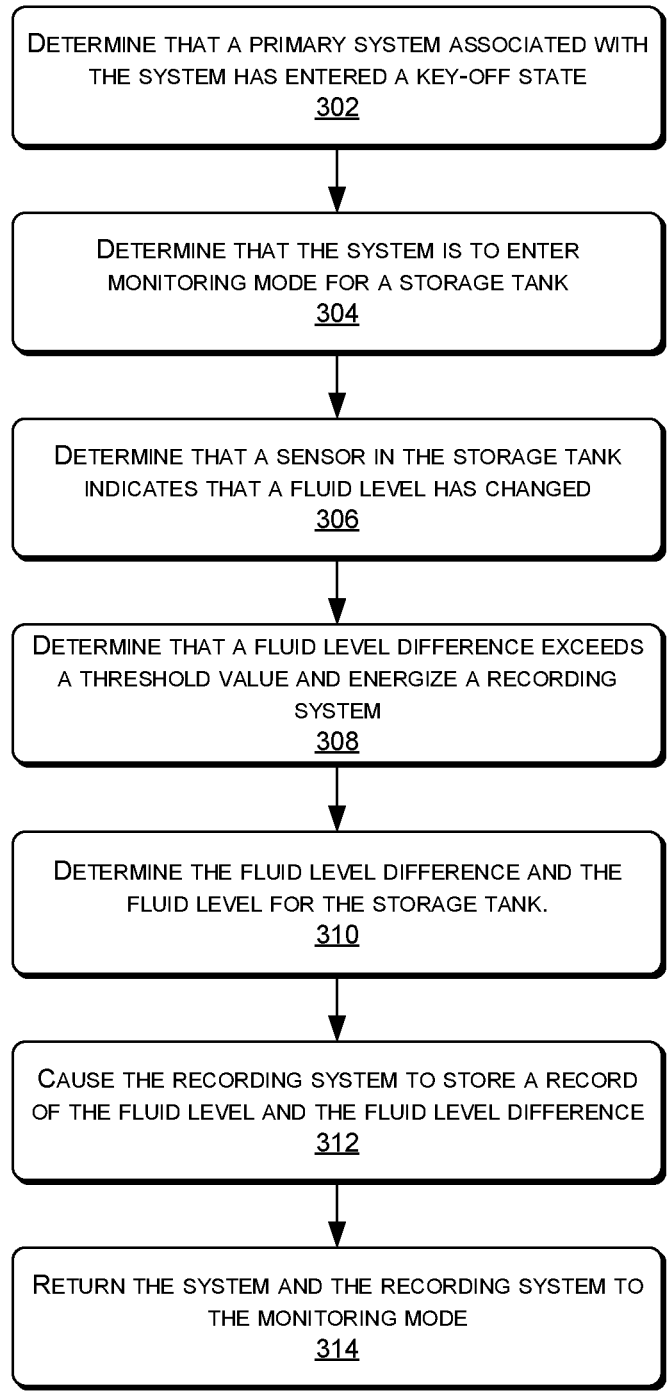
FIG. 3 is a block diagram illustrating a method for monitoring a storage tank according to examples of the present disclosure where the system is transitioned from an active state to an inactive state.

FIG. 3 is a block diagram of a method 300 according to examples of the present disclosure. The method 300 can be executed by a low power circuit associated with a tank controller 128 as shown and described above with respect to FIG. 2. Additionally, any of the methods described herein may be performed in whole, or in part, by the one or more processors 218 associated with the tank controller 128 and/or other control devices associated with the storage tank 202.

At 302, the processor 218 (and/or the low power circuit 220) can be configured to determine that the primary systems 222 associated with the system have entered a key-off state. In particular, the processor 218 can be configured to detect a current state of the circuit switch 224, wherein the current state of the circuit switch 224 can indicate that the primary systems 222 are in a key-on state where the primary systems 222 are activated or that the primary systems 222 are in the key-off state where the primary systems 222 are deactivated. The primary systems 222 can be associated with a power source 226 that is connected to at least two circuits associated with the processor 218 and/or the tank controller 128. For instance, a switched power circuit 228 can be configured to provide power to the primary systems 222, the tank controller 128, and components of the tank controller 128 (e.g., the processor 218 and/or the low power circuit 220) during the key-on state and deactivate during the key-off state. Additionally, a direct power circuit 230 can be configured as a low power circuit that is configured to substantially continuously provide power to a monitoring system (e.g., the low power circuit 220) and/or the processor 218 during at least the key-off state. Further, the processor 218 can determine that the system has entered a key-off state based on an indication received from the circuit switch 224 and determining that the state of the circuit switch 224 has been modified. Accordingly, the processor 218 can determine that the switched power circuit 228 is no long providing power and receive an indication that the primary systems 222 have been deactivated.

At 304, the processor 218 (and/or the low power circuit 220) can be configured to determine that the system is to enter monitoring mode for a storage tank 202. In particular, the processor 218 can determine that the system has entered the key-off state, and initiate monitoring the storage tank 202 associated with the processor 218 via the low power circuit 220 and/or the fluid level sensor 206. Additionally, the storage tank 202 can be associated with a fluid that is to be maintained above a threshold associated with fluid quality (e.g., fluid concentration, fluid purity, etc.) and one or more sensors that are configured to obtain one or more fluid variables. Further, the CAN 212 can be configured to provide communication between the processor 218 and the fluid level sensor and provide power from the direct power circuit 230 to at least the fluid level sensor 206 associated with the storage tank 202 such that the low power circuit 220 receives one or more indications of the fluid level within the storage tank 202 during the key-off state.

At 306, the processor 218 (and/or the low power circuit 220) can determine that the fluid level sensor 206 in the storage tank 202 indicates that a fluid level has changed. In particular, the fluid level sensor 206 can be configured to determine a current fluid level within the storage tank 202 and transmit the current fluid level to the processor 218 via the low power circuit 220. Additionally, the processor 218 (and/or the low power circuit 220) can receive an initial fluid level for the storage tank 202 during a period of time where the circuit switch 224 causes the switched power circuit 228 to provide power to the tank controller 128 and/or during a transition from the key-on state to the key-off state by the circuit switch 224. More specifically, during operation of the primary systems 222 and the key-on state, the fluid level sensor 206 can be configured to substantially continuously, periodically, aperiodically, and/or otherwise provide the fluid level within the storage tank 202 to the processor 218 on a substantially scheduled basis (e.g., based on a monitoring schedule). The fluid level sensor 206 can also be configured to provide the fluid level within the storage tank 202 upon request, in response to the processor 218 detecting a trigger event, or otherwise causing the fluid level sensor 206 to report the fluid level within the storage tank 202. Alternatively, or in addition, the processor 218 can receive an indication from the circuit switch 224 and/or the primary systems 222 that indicates a transition from the key-on state to the key-off state has occurred, wherein the processor 218 can cause the fluid level sensor 206 to determine and provide the fluid level within the storage tank 202 in response to the indication of the transition. Accordingly, the processor 218 can receive an indication of an initial fluid level within the storage tank 202.

In some examples, the processor 218 (and/or the low power circuit 220) can determine that the fluid level is to be determined by the fluid level sensor 206 after an amount of time has elapsed. Similar to the above paragraph and during the key-off state, the direct power circuit 230 can be configured to provide power to the fluid level sensor 206, via the CAN 212. Additionally, the processor 218 can provide a request for the fluid level to the fluid level sensor 206 on a substantially continuously, periodically, aperiodically, and/or other basis that enables the processor 218 to determine whether the storage tank 202 has been tampered with or otherwise altered. Accordingly, the processor 218 can cause the fluid level sensor 206 to report the fluid level to the processor 218. Additionally, the processor 218 can compare a current fluid level (e.g., the most recently received fluid level) with the initial fluid level and/or a set of the preceding fluid levels (e.g., the fluid levels received by the processor since entering the key-off state) to determine that the fluid level within the storage tank 202 has changed. In at least one example, the processor 218 can be configured to determine a rate of change for the fluid level within the storage tank based at least on a set of fluid levels determined by the fluid level sensor 206 206. In particular, the detection of a non-zero rate of change for the fluid level within the storage tank 202 over a period of time can indicate that the fluid level has changed and/or is changing.

At 308, the processor 218 (and/or the low power circuit 220) can determine that a fluid level difference exceeds a threshold value and energy a recording system. In particular, the processor 218 can utilize the current fluid level and the initial fluid level/the set of the preceding fluid levels to determine the fluid level difference. The fluid level difference can be an indicator of a magnitude of fluid level change within the storage tank 202 over a period of time. Additionally, a threshold value can be associated with the fluid level difference such that a determination that the fluid level difference exceeds the threshold value can cause the processor 218 to activate a recording system. More specifically, the processor 218 can cause, based at least on the determination that the fluid level difference exceeds the threshold value, the direct power circuit 230 to provide power to the recording system, via the CAN 212, and activate the recording system such that a record of the fluid level difference exceeded the threshold value is generated.

At 310, and based at least on the fluid level has reached a stable state, the processor 218 (and/or the low power circuit 220) can determine a stable fluid level and a total fluid level difference from the initial fluid level to the stable fluid level within the storage tank 202. In particular, the processor 218 can be configured to monitor the fluid level within the storage tank 202, via the fluid level sensor 206, while the fluid level is changing to determine the rate of change for the fluid level and the magnitude of the fluid level difference. For example, the processor 218 can transmit one or more requests for the current fluid level over a period of time until the fluid level within the storage tank 202 reaches the stable fluid level (e.g., transmitting the one or more requests until the current fluid level received from the fluid level sensor 206 reports the stable fluid level for a number of sequential fluid levels to the processor 218). Alternatively, or in addition, the processor 218 can schedule a series of periodic fluid level measurements, monitor the fluid levels reported by the fluid level sensor 206 during the series of periodic fluid level measurements, and determine the stable fluid level for the fluid within the storage tank 202. Additionally, the processor 218 can be configured to monitor the rate of change for the fluid level based at least on a set of fluid levels determined by the fluid level sensor 206 and transmitted to the processor 218. Independent of how the stable fluid level is determined, the processor 218 may determine the stable fluid level and a total fluid level difference for the storage tank 202. Further, the processor 218 can be configured to capture rate of change data for the fluid level over the period of time to capture modifications made to the fluid level within the storage tank 202 that results in a net zero total fluid level difference (e.g. the same amount of fluid is output as input into the storage tank 202.

At 312, the processor 218 (and/or the low power circuit 220) can cause the recording system to generate a record of the stable fluid level and the total fluid level difference. In particular, the processor 218 can transmit an indication of the stable fluid level, the total fluid level difference, and associated data to the recording system and cause the recording system to generate the record of the stable fluid level, the total fluid level difference, whether the total fluid level difference triggers a fluid composition determination. Additionally, the processor can cause the direct power circuit 230 to provide power to one or more additional sensors 214 and obtain one or more additional storage tank variables associated with the fluid stored by the storage tank 202. Alternatively, or in addition, the recording system can be the tank controller 128, wherein the processor 218 transmits a wake-up signal to the tank controller 128 and causes the tank controller 128 to provide power, via the direct power circuit 230, to the one or more additional sensors 214 and record the one or more additional storage tank variables associated with the fluid. Accordingly, the recording system can generate the record describing the stable state of the fluid within the storage tank 202 while the primary systems 222 are in the key-off state.

At 314, the processor 218 (and/or the low power circuit 220) can return the system and the recording system to the monitoring mode. In particular, the processor 218 can deactivate the recording system (or the tank controller 128 can deactivate itself after generating the record) and return the fluid level sensor 206 to standard monitoring measurements. Additionally, the processor 218 can be configured to update the initial fluid level to the value of the stable fluid level.

Accordingly, the method 300 can enable the tank controller 128 and/or components of the tank controller 128 to determine whether a potential tampering event has occurred based on fluid levels detected by the fluid level sensor 206. More specifically, the low power circuit 220 (or the processor 218) can be configured to receive a first fluid level and a second fluid level, determine a fluid level difference, and determine whether the fluid level difference exceeds a threshold value that is associated with a potential tampering event. Further, the fluid level difference exceeding the threshold value can trigger the generation of a record, stored by memory 216, that triggers a fluid verification process upon the primary systems 222 transitioning from a key-off state to a key-on state.

Figure 4:
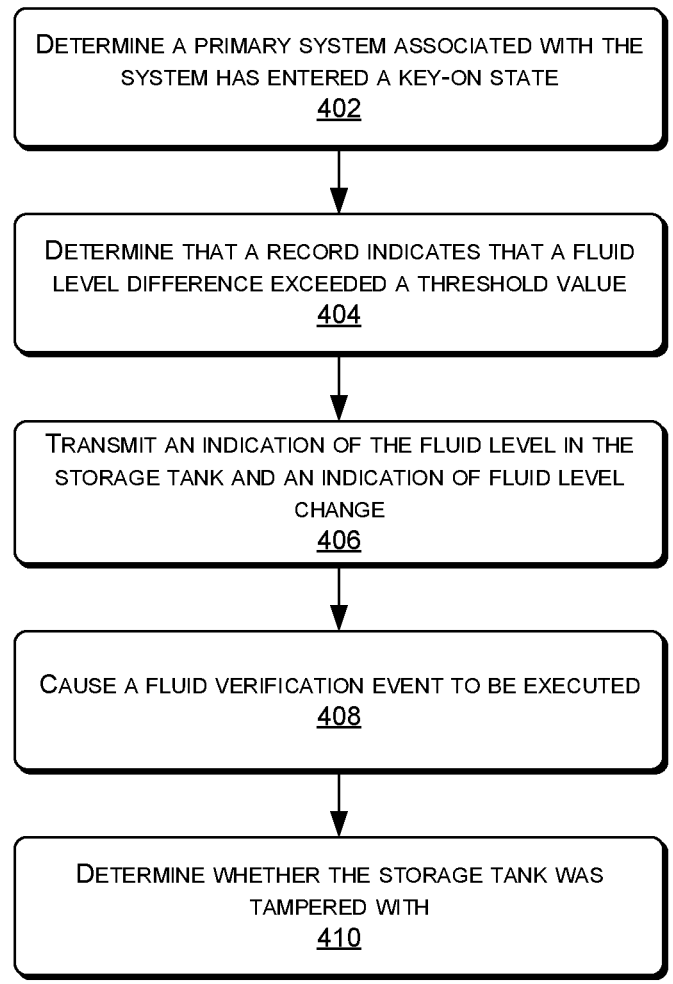
FIG. 4 is a block diagram illustrating a method for monitoring a storage tank according to examples of the present disclosure where the system is transitioned from an inactive state to an active state.

FIG. 4 is a block diagram of a method 400 according to examples of the present disclosure. The method 400 can be executed by a low power circuit associated with a tank controller 128 as shown and described above with respect to FIG. 2. Additionally, any of the methods described herein may be performed in whole, or in part, by one or more processors associated with the tank controller 128 and/or other control devices associated with the monitoring system. Unless otherwise noted, such processor(s) will be described for the remainder of this disclosure without reference to the tank controller 128, the processors 218, the low power circuit 220, and/or other control devices noted above. Further, the method 400 can continue from block 304 of the method 300 and describes startup operations for a monitoring system.

At block 402, the processor 218 (and/or the low power circuit 220) determining that the system is to enter a monitoring mode for a storage tank 202, the processor 218 can determine that the primary systems 222 associated with the system have entered a key-on state. In particular, the processor 218 can receive an indication from the circuit switch 224 and/or the primary systems 222 that the circuit switch 224 has been updated from the key-off (deactivated) state to a key-on (activated) state. Additionally, the processor 218 can determine, based at least on the indication, that the tank controller 128 and the components of the tank controller 128 are to receive power from the switch power circuit 228 associated with the primary systems 222.

At block 404, the processor 218 (and/or the low power circuit 220) can determine that a record system indicates that the system detected a fluid level difference exceeding a threshold. In particular, the recording system can include a record that was generated during the key-off state based at least on an indication provided by the processor 218. The record can indicate that the recording system was activated by the processor 218 (and/or tank controller 128) and can indicate that a fluid composition check is to be performed based at least on the fluid level difference detected by the fluid level sensor 206 while the circuit switch (and the primary systems 222) were in the key-off state. Additionally, one or more additional records may include additional indications of the fluid level in the storage tank 202 and the fluid level difference associated with one or more additional indications provided by the processor 218. Further, the record and the one or more additional records may include additional storage tank variables such as temperature of the fluid (e.g., a storage tank temperature), pressure within the storage tank 202 (e.g., a storage tank pressure), and other related storage tank variables. The additional storage tank variables can be determined based sensor data received from one or more additional sensor associated with the storage tank (e.g., storage tank temperature determined from sensor data generated by a thermocouple, storage tank pressure determined from sensor data generated by a pressure sensor, etc.) It should be noted that while the above discussion has been primarily related to the determination of fluid level, similar processes can be utilized to identify abnormal temperature readings (e.g., the processor 218 causes the direct power circuit 230 to provide power to a thermocouple or other temperature reading device that determines and reports a temperature within the storage tank such that the processor can determine whether abnormal heating/cooling of fluid in storage tank 202 has occurred), abnormal pressure readings, and/or other variations in system variables of the storage tank 202 that deviate from a steady state of the storage tank 202 (e.g., steady state fluid level, steady state temperature, steady state pressure, etc.). Accordingly, the record generated by the record system can include indications of abnormal system variable readings that cause the tank controller 128 to perform and/or trigger verification processes for the fluid within the storage tank 202.

At block 406, the processor 218 (and/or the low power circuit 220) can receive the record from the recording system (e.g., from the memory 216) and transmit the record to a fluid verification system. In particular the processor can be configured to cause the record to be transmitted to a verification system that is configured to perform the fluid composition check, a fluid concentration check, an operating effectiveness check, and other verification tests that are configured to ensure that the fluid within the storage tank 202 satisfies one or more thresholds associated with fluid composition and treatment efficacy. Additionally, the processor 218 can transmit the record associated with indications of the fluid levels, the fluid level difference, the fluid level velocity at a time, fluid temperature (or storage tank temperature, storage tank 202 pressure, and/or other system variables to assist in the verification of the fluid in the storage tank 202.

At block 408, the processor 218 (and/or the low power circuit 220) can cause a fluid quality check to be executed. In particular, the record and the indication that the fluid level difference exceeded the threshold value can cause the verification system to perform a fluid quality check and determine whether the fluid in the storage tank 202 satisfies one or more thresholds associated with the fluid. For example, the fluid quality check can be a DEF verification that is performed by the verification system, wherein the verification system is a DEF concentration sensor configured to determine a DEF concentration that can be utilized to determine whether the DEF concentration of the fluid within the storage tank 202 satisfies a DEF concentration threshold (e.g., a minimum DEF concentration). More generally, the verification system can be configured to determine whether a composition of the fluid satisfies one or more compositional standards (e.g., have any impurities been added to the fluid), whether a concentration of the fluid satisfies one or more concentration standards (e.g., are the active compounds within the fluid at a desired concentration), and other determinations related to efficacy of the fluid in the instant application (e.g., confirming that DEF is of sufficient purity and concentration to convert pollutants to innocuous gases). Accordingly, the verification system can be configured to determine whether the fluid has been tainted with impurities and/or been diluted below a concentration threshold. Further, the verification system can be configured to update the record to include an indication of whether the fluid includes impurities and/or whether the fluid has a concentration outside of an approved range.

At block 410, the processor 218 (and/or the low power circuit 220) can determine whether the storage tank 202 was tampered with. In particular, the processor 218 can receive, from the verification system, and indication of the fluid concentration and/or the fluid composition and determine whether the fluid satisfies one or more thresholds (e.g., composition thresholds, concentration thresholds, etc.). Accordingly, the processor 218 can determine that maintenance is to be provided and/or transmit a maintenance request and/or notification to an administrator that the storage tank 202 is to be replenished, provided maintenance, and/or otherwise be assigned a task for resolving the fluid composition and/or the fluid composition satisfying one or more thresholds configured to indicate that the fluid is outside of operational parameters for the primary systems 222.

Figure 5:
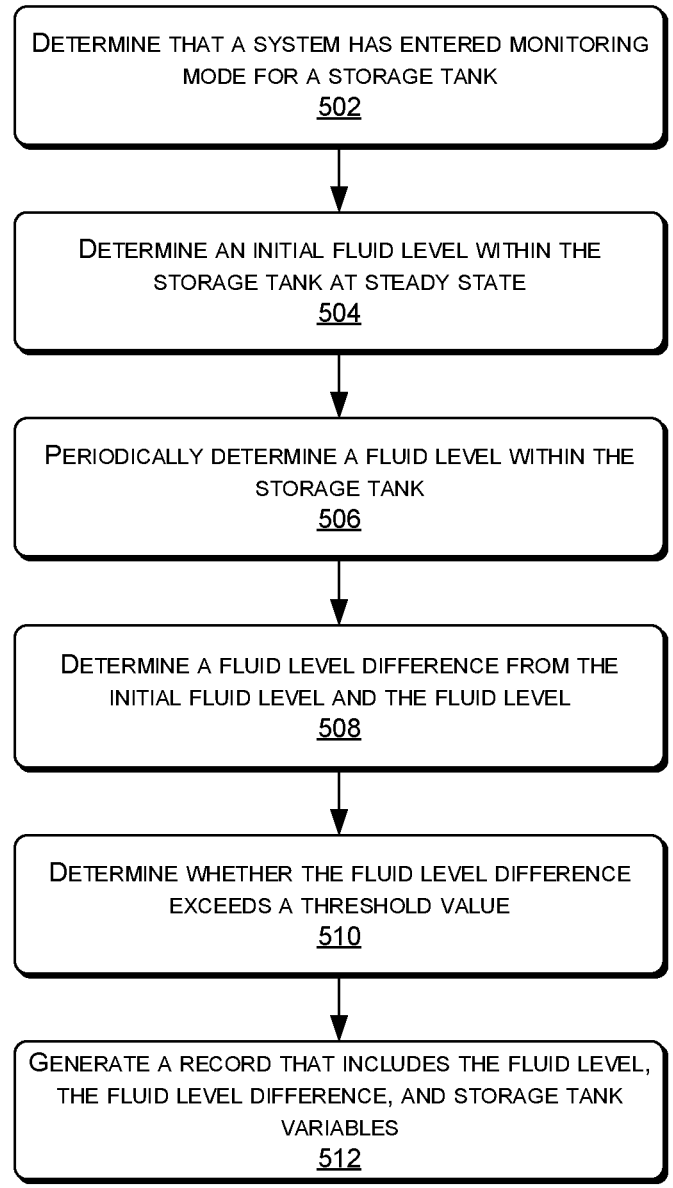
FIG. 5 is a block diagram illustrating a method for monitoring a storage tank according to examples of the present disclosure where the system configured to monitor fluid within a storage tank.

FIG. 5 is a block diagram of a method 500 according to examples of the present disclosure. The method 500 can be executed by a low power circuit 220 associated with a tank controller 128 as shown and described above with respect to FIG. 2. Additionally, any of the methods described herein may be performed in whole, or in part, by one or more processors (including the processors 218) associated with the tank controller 128 and/or other control devices associated with the monitoring system.

At block 502, a processor (e.g., a microprocessor, a micro controller, a CPU, etc.) of the low power circuit 220 (e.g., a first controller) can determine that a system has entered monitoring mode for a storage tank 202. In particular, the processor can be configured to determine that the primary system 222 has entered a key-off state. In particular, the processor can be configured to detect a current state of a circuit switch 224, wherein the current state of the circuit switch 224 can indicate that the primary system 222 is in a key-on state where the primary system 222 is activated or that the primary system 222 is in the key-off state where the primary system 222 is deactivated. The primary system 222 can be associated with a power source 226 that provides power via at least two circuits associated with the system. For instance, a switched power circuit 228 can be configured to provide power to the primary systems 222, a tank controller 128 associated with the low power circuit 220, the processor of the low power circuit 220, and/or other components associated with the tank controller 128 (e.g., the processor 218, the fluid level sensor 206, etc.) during the key-on state and deactivate during the key-off state. Additionally, a direct power circuit 230 can be configured as a low power circuit that is configured to substantially continuously provide power to the low power circuit and the processor of the low power circuit 220 during the key-off state and/or the key-on state. Further, the processor can determine that the system has entered a key-off state based on an indication received from the circuit switch 224, based on an indication that the state of the primary systems 222 has been modified, based on a determination that the switched power circuit 228 is no long providing power, and other indications that the primary system has been deactivated.

In some additional examples, the direct power circuit 230 and the switched power circuit 228 can be configured to provide power from the power source 226 to the tank controller 128, the processor 218, the low power circuit 220, and/or the primary systems 222 associated with the primary system. In particular, the switched power circuit 228 can be configured to provide substantially sufficient power that enable the primary system of the primary systems 222, the fluid level sensor 206, one or more additional sensors 214, the tank controller 128, and other components of the tank controller 128. Additionally, the direct power circuit 230 can be configured to provide an amount of power that at least satisfies a power demand associated with the fluid level sensor 206, the low power circuit 220, and a controller area network (CAN) 212 between the fluid level sensor 206 and the low power circuit 220. Further, the direct power circuit 230 satisfy additional power demands associated with systems that have received a wake-up signal from the low power circuit 220 and/or the processor of the low power circuit 220. Accordingly, the direct power circuit 230 can enable the fluid level sensor 206, the low power circuit 220, and the CAN 212 to continue operation while the primary systems are in the key-off state and enable operation of additional systems and/or components in response to wake-up signals transmitted by the low power circuit 220.

At block 504, the processor of the low power circuit 220 can cause the fluid level sensor 206 to determine an initial fluid level within the storage tank 202 at steady state (e.g., a steady state fluid level). In particular, the low power circuit 220 can transmit an activation command to the fluid level sensor 206 that causes the fluid level sensor 206 to determine the initial fluid level. The activation command can also be transmitted to the power source 226 and/or the direct power circuit 230 and cause the power source 226 and/or the direct power circuit to provide power to the fluid level sensor 206. The initial fluid level within the storage tank 202 can be associated with an amount of fluid within the storage tank 202 that is stored at an initial temperature and/or an initial pressure when the primary systems 222 enter the key-off state. Additionally, the initial fluid level can be determined based on one or more fluid level measurements to determine that the storage tank 202 exists at substantially steam state (e.g., initial system variables including volume of fluid, storage tank pressure, storage tank temperature and other initial system variables are approximately constant over a period of time. Accordingly, the initial fluid level and the associated system variables can be determined for the processor during a period of time. It should be noted that the processor and the low power circuit 220 can be in communication with the fluid level sensor 206 and cause the direct power circuit 230 to provide power to the fluid level sensor 206 via the CAN 212.

In some examples, the fluid level sensor 206 can include a float that is configured to float on a surface of the fluid within the storage tank 202. Additionally, the fluid level sensor 206 can include a fluid level sensor support 208 that extends substantially parallel the longitudinal axis 232 and enables the float to travel along the longitudinal axis 232. The float may be associated with a track that allows the flow to travel the length of the fluid level sensor support 208 and/or may include a hole that enables the float to be mounted onto the fluid level sensor support 208. Further, the fluid level sensor 206 may include one or more fluid level detectors that are configured to detect a position of the fluid level sensor 206 on the fluid level sensor support 208. The one or more fluid level detectors can be one or more fluid level triggers 208a that are configured to detect when the float is in proximity to the fluid level triggers 208a and/or dynamic detectors that are configured to determine a position of the float on the fluid level sensor 206 support. Accordingly, a fluid sensor interface can be utilized to establish the communication link with the CAN 212 and can be configured to receive a signal from the fluid level detector, convert the signal into an indication of the amount of fluid in the storage tank 202, and transmit the indication to the system.

At block 506, the processor of the low power circuit 220 can periodically receive an indication of a fluid level within the storage tank 202 based at least in part on a monitoring schedule. In particular, the processor can be configured to request, from the fluid level sensor 206, the fluid level within the storage tank 202 on a substantially continuous, periodic, aperiodic, and/or other basis. More specifically, the processor can transmit the activation signal to the fluid level sensor 206, transmit a fluid level request to the fluid level sensor that requests a determination of the fluid level within the storage tank 202, receive an indication of the fluid level within the storage tank 202, and transmit a deactivation command to the fluid level sensor 206. Additionally, the fluid level sensor 206 can be configured to receive the request, determine the fluid level, generate the indication of the fluid level, and transmit the fluid level to the processor. Further, the processor can be configured to receive additional indications of additional system variables from one or more additional sensors 214 associated with the fluid level at the current time. Similar to the fluid level, the processor can transmit additional requests to additional sensors 214 that cause the additional sensors 214 to determine the additional indications and transmit the additional indications to the processor.

At block 508, the processor can determine a fluid level difference from the initial fluid level and the fluid level at the current time. Similarly, at block 510, the processor can determine whether the fluid level difference exceeds a threshold value. The process of block 508 and 510 can be accomplished in a manner similar to that discussed above with respect to FIGS. 1-4. It should be noted that determining the fluid level difference from the initial fluid level (e.g., a first fluid level) and the fluid level at the current time (e.g., a second fluid level) can be performed by a low power logic circuit (e.g., the low power circuit 220) via a logic gate or other comparator configured to compare the initial fluid level and the fluid level at the current time and output an indication of the fluid level difference. Alternatively, or in addition, determining the fluid level difference can be executed by a microprocessor or the processor of the low power circuit 220, wherein the low power circuit 220 is configured to determine the difference and generate an indication of the difference.

At block 512, the processor of the low power circuit 220 can cause the tank controller 128 and/or the memory 216 to generate a record that includes the fluid level, the fluid level difference, and/or the additional system variables. In particular, the tank controller 128 can include the memory 216 that is configured to receive, from the processor, an indication that the fluid level difference within the storage tank 202 exceeds a threshold value. Additionally, the processor can cause the memory 216 to generate, based at least on the fluid level difference detected exceeding the threshold value, the record that indicates that fluid verification is to occur in response to a transition from the key-off state to the key-on state by the primary systems 222. Further, the processor can cause the record to be generated to include the fluid level, the fluid level difference, and the storage tank 202 variables to record operation variables of the storage tank 202.

In some examples, the processor of the low power circuit 220 can be configured to utilize the CAN 212 to transmit a wake-up signal to one or more addition systems associated with the processor, such as the tank controller 128 (e.g., a second controller). In particular, the processor can transmit the wake-up signal to and cause the CAN 212 to transmit power to the tank controller 128, to the processor 218 of the tank controller 128, to the memory 216, to a fluid evaluation system (e.g., a DEF composition sensor), and/or other systems that facilitate a determination of whether the fluid within the storage tank 202 has been modified. Additionally, the wake-up signal can be transmitted to cause the tank controller 128 (e.g., via the memory 216) to generate the record of the potential modification of the fluid such that the record can cause the tank controller 128, upon transition from the key-off state to the key-on state by the primary systems 222, to trigger verification of the fluid via at least a composition check and/or a concentration check of the fluid within the storage tank 202. Similarly, the record can cause the fluid evaluation system to determine whether the composition and/or the concentration of the fluid within the storage tank 202 satisfies a composition threshold and/or a concentration threshold. Accordingly, the low power circuit 220 (e.g., the low power circuit 220) can be configured to determine whether the fluid in the storage tank 202 has been modified and cause a notification to be transmitted by the tank controller 128 requesting maintenance and/or intervention where the fluid has been modified to no longer comply with the composition threshold and/or the concentration threshold.

Figure 6:
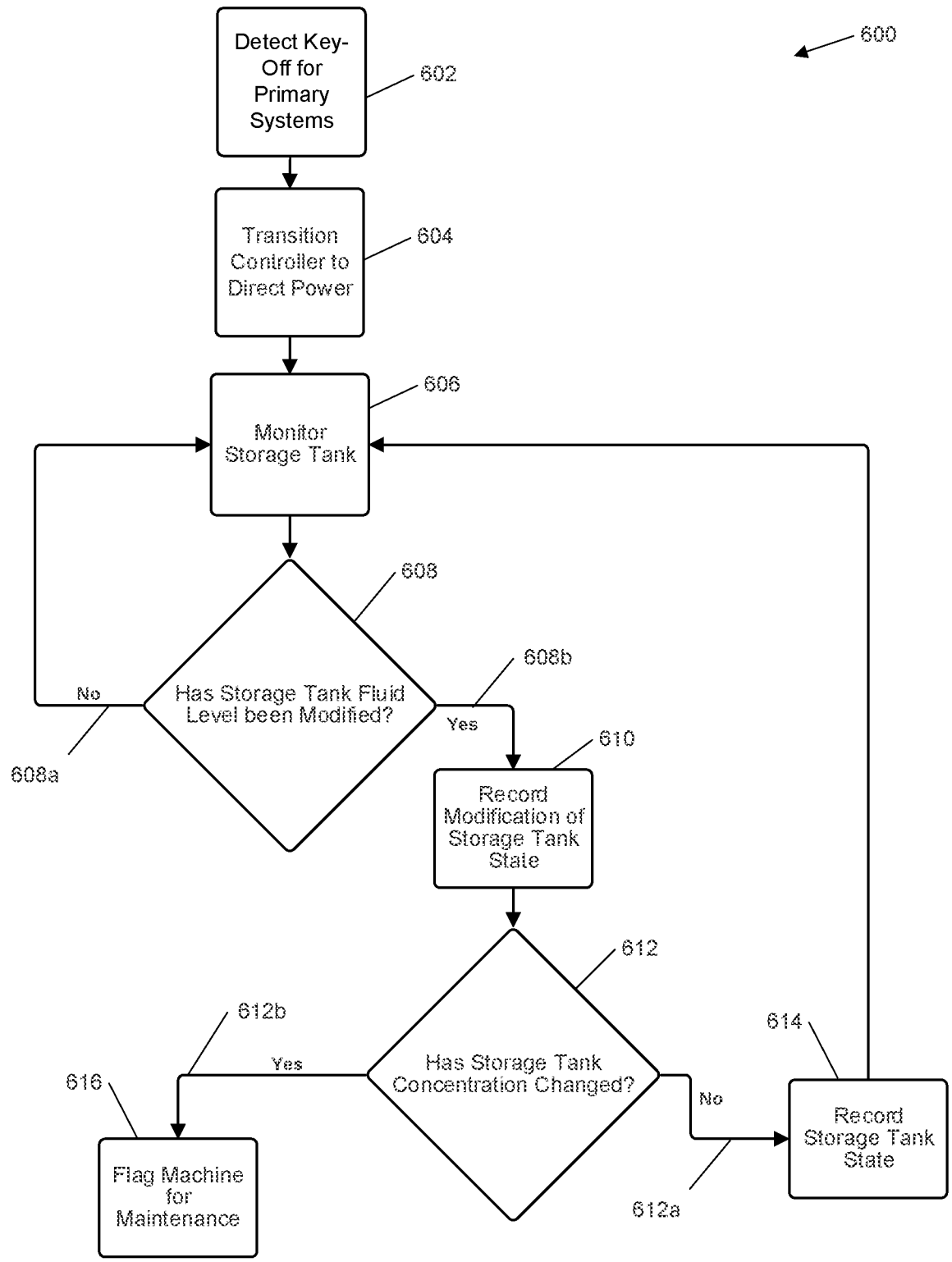
FIG. 6 is a block diagram of a decision tree executed by a monitoring system configured to monitor DEF within a storage tank.

FIG. 6 is a block diagram of a decision tree executed by a monitoring system configured to monitor DEF within a storage tank 202. In particular, the decision tree illustrated by FIG. 6 can indicate a baseline decision tree for monitoring DEF within a storage tank 202.

At block 602, the tank controller 128 or other controller associated with one or more primary systems 222 can detect that the one or more primary systems 222 have received a key-off command that terminates power transmission via the switched power circuit 228 associated with the primary systems 222. Additionally, the power source 226 associated with the one or more primary systems 222 may be unable to recharge itself during the key-off state. Accordingly, the tank controller 128 can be configured to minimize power consumption via the direct power circuit 230 while monitoring the storage tank 202 during the key-off state.

At block 604, a tank controller 128 can be transitioned from switched power circuit 228 of the primary systems 222 to a direct power circuit 230 with the power source 226. In particular, the tank controller 128 can be configured to draw power from the power source 226 to monitor the DEF within the storage tank 202 via the direct power circuit 230. Additionally, the tank controller 128 or a component of the tank controller 128 (e.g., the processor 218 and/or the low power circuit 220) can be configured to cause the direct power circuit 230 to provide power from the power source 226, via the CAN 212, to a fluid level sensor 206 within the storage tank 202. More specifically, the low power circuit 220 or another component of the tank controller 128 (e.g., the processor 218) can receive power from the direct power circuit 230 and transmit, via the CAN 212, a request for a fluid level to the fluid level sensor 206 that activates the fluid level sensor 206 and causes the fluid level sensor 206 to determine the fluid level within the storage tank 202. Additionally, the low power circuit 220 can receive the fluid level from the fluid level sensor 206 and deactivate the fluid level sensor 206 for a period of time determined on the monitoring basis for the DFE (e.g., continuous equals substantially no time between fluid level measurements, periodic pauses a set amount of time between fluid level measurements, and aperiodic pauses for a variable amount of time between fluid level measurements). Accordingly, the tank controller 128 and/or the components of the tank controller 128 can be configured to cause the fluid level sensor 206 to provide one or more fluid levels to the controller. Further, the tank controller 128 can be configured to monitor the storage tank 202, as noted by block 606, via the fluid level sensor 206.

At block 608, the tank controller 128 can determine whether the fluid level within the storage tank 202 has been modified. In particular, the tank controller 128 or a processor of the tank controller 128 (e.g., the processor 218 and/or a processor of the low power circuit 220) can be configured to determine whether the fluid level within the storage tank 202 has been modified relative to an initial fluid level determined while the tank controller 128 was receiving power via the switched power circuit 228 and/or when the tank controller 128 received power via the direct power circuit 230. Additionally, the tank controller 128 can be configured to identify any variation in the fluid level and/or identify a fluid level difference (e.g., a difference between a measured fluid level and the initial fluid level) that exceeds a threshold value. Accordingly, and based at least on the basis for identifying modification of the fluid level within the storage tank 202, the tank controller 128 can be configured to determine that the fluid level within the storage tank 202 has been modified or that the fluid level has not been modified. It should be noted that where the fluid level has not been modified, the tank controller 128 can resume monitoring the storage tank 202 at block 606 (via path 608a).

In contrast, and via path 608b, the tank controller 128 can be configured to generate a record of the modification of the storage tank 202 state at block 610. In particular, the tank controller 128 can be configured to record, via the memory 216, that the fluid level difference determined by the controller exceeded the threshold value. The threshold value can represent a volume difference, a percentage of tank volume difference (e.g., 5% difference in tank fill volume), a mass difference, or other difference detectable by the fluid level sensor 206 and/or other sensors associated with the storage tank 202. Additionally, the tank controller 128 can cause an indication to be recorded, via the memory 216 that is configured to notify a fluid evaluation system that a fluid evaluation check is to be performed. The controller can transmit the indication to the fluid evaluation system based at least on a transition of the circuit switch 224 from the key-off state to the key-on state. More specifically, the determination that the fluid level difference exceeds the threshold value can cause the tank controller 128 to trigger a fluid evaluation check to determine whether a fluid composition and/or a fluid concentration satisfy a fluid composition threshold(s) and/or a fluid concentration threshold(s).

At block 612, the fluid evaluation system can be provided the indication and/or the record to initiate a determination of whether the fluid within the storage tank 202 been modified to alter a DEF concentration and/or a DEF composition. Where the fluid evaluation system determines that the DEF concentration and/or the DEF composition does not satisfy the fluid composition threshold(s) and/or fluid concentration threshold(s), the controller can issue a notification that flags the storage tank 202 for maintenance via path 612b to block 616. In contrast, where the DEF concentration and/or the DEF composition does satisfy the fluid composition threshold(s) and/or fluid concentration threshold(s), the controller can proceed via path 612a to block 614. The current fluid level of the DEF in the storage tank 202, the DEF concentration, the DEF composition, and other values can be recorded as an expected state for the DEF against which future monitoring by the controller is compared against.

INDUSTRIAL APPLICABILITY

The present disclosure describes systems and methods for monitoring a storage tank for DEF to prevent modification, diluting, and/or tainting of the DEF stored by a system. The example systems and methods described herein can be used with SCR systems for internal combustion-type motors, and the disclosed systems are configured maintain substantially continuous monitoring of the storage tank and the DEF within. A monitoring device can include a storage tank, a fluid level sensor 206, a controller, and a power source. Additionally, the monitoring device can include a recording system, one or more additional sensors 214, a verification system that includes a DEF composition sensor and a DEF concentration sensor, and other supplementary systems. The storage tank 202 can be configured to store DEF for consumption by a selective SCR system and can comprise: a first wall, a second wall substantially parallel to the first wall, a longitudinal axis 232 that extends substantially centrally through the storage tank from the first wall to the second wall, and at least a third wall substantially perpendicular to the first wall and the second wall. Further a fluid level sensor 206 can be configured to indicate an amount of DEF that is stored within the storage tank, wherein the fluid level sensor 206 can be attached to the first wall of the storage tank and extend substantially parallel to the longitudinal axis 232 within the storage tank. The controller can be configured to monitor the amount of DEF that is stored within the storage tank via a communication link with the fluid level sensor 206. Similarly, the power connection between the controller associated with the fluid level sensor 206 and a power source can be configured to provide operating power for the controller and the fluid level sensor 206 during a key-off state of the SCR system. Accordingly, the monitoring device can be configured to maintain monitoring operations associated with the fluid in the storage tank while the power source is shut off for the primary systems associated with the monitoring device.

While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

The invention claimed is:

1. A system, comprising:
a storage tank configured to store an amount of diesel exhaust fluid (DEF), and fluidly connected to a selective catalytic reduction (SCR) system;
a fluid level sensor configured to determine the amount of DEF disposed within the storage tank, wherein the fluid level sensor is configured to generate first information indicating a first amount of DEF within the storage tank at a first time, and second information indicating a second amount of DEF within the storage tank at a second time;
a controller in communication with the fluid level sensor, the controller being configured to:
receive the first information and the second information,
determine a difference between the first amount and the second amount based on the first information and the second information, and
generate an indication that the difference exceeds a threshold value;
a power source operably connected to a direct power circuit and a switched power circuit, the direct power circuit being configured to supply power from the power source to the controller and the fluid level sensor during a key-off state of the SCR system, wherein the direct power circuit supplies the power to the controller and the fluid level sensor at the second time; and
the switched power circuit being configured to supply power from the power source to the controller and the fluid level sensor during a key-on state of the SCR system.

2. The system of claim 1, wherein the direct power circuit is configured to:
provide first power to the controller that exceeds a controller power demand;
provide second power to the fluid level sensor that exceeds a fluid sensor power demand; and
provide third power to a memory and one or more additional sensors based at least in part on a wake-up signal transmitted by the controller.

3. The system of claim 1, further comprising a controller area network configured to transmit:
one or more fluid level requests from the controller to the fluid level sensor,
the first information and the second information to the controller, and
the power from the power source to at least the fluid level sensor via the controller.

4. The system of claim 1, wherein the fluid level sensor comprises:
a float sensor that is configured to float on the DEF within the storage tank;
a fluid level detector that is configured to detect a position of the float sensor within the storage tank; and
a fluid sensor interface configured to receive a signal from the fluid level detector, determine the first amount based on the signal, and transmit the first information to the controller.

5. The system of claim 1, wherein the controller further comprises a low power circuit in communication with the fluid level sensor, wherein the low power circuit is configured to:
receive the power from the direct power circuit while the SCR system is in the key-off state;
cause the fluid level sensor to determine the first amount and the second amount; and
determine that the difference exceeds the threshold value, the low power circuit being configured to generate a wake-up signal that activates the controller and causes the controller to generate the indication based on the difference exceeding the threshold value.

6. The system of claim 5, wherein the wake-up signal causes:
the direct power circuit to provide the power from the power source to a processor of the controller;
the processor to receive the first information and the second information and determine that the difference exceeds the threshold value;
the processor to request sensor data from one or more additional sensors associated with the storage tank; and
the processor to store at least the difference, the indication, and the sensor data.

7. The system of claim 1, further comprising:
a memory configured to store the difference and the indication, wherein the indication triggers determination of a DEF concentration for the second amount of DEF within the storage tank; and
a DEF concentration sensor configured to, based at least on the indication stored by the memory, determine the DEF concentration corresponding to the second amount, wherein the controller is configured to:
receive third information indicative of the DEF concentration from the DEF concentration sensor,
determine that the DEF concentration satisfies a DEF concentration threshold, and
transmit a maintenance request to an administrator based at least on determining that the DEF concentration satisfies the DEF concentration threshold.

8. The system of claim 1, wherein the controller is configured to receive the power via the direct power circuit while the SCR system is in the key-off state and cause the fluid level sensor to generate the first information and the second information while the SCR system is in the key-off state.

9. A method, comprising:
determining, with a low power circuit, that a primary system associated with a storage tank has entered a key-off state;
based at least in part on determining that the primary system has entered the key-off state, causing, with the low power circuit, a fluid level sensor within the storage tank to determine:
a first fluid level of a fluid within the storage tank at a first time, and
a second fluid level of the fluid within the storage tank at a second time;
determining, with the low power circuit, that a difference between the first fluid level and the second fluid level exceeds a threshold;
based at least in part on determining that the difference exceeds the threshold, transmitting, with the low power circuit and to a direct power circuit operably connected to a power source, a command causing the direct power circuit to provide power from the power source to a tank controller, wherein the tank controller generates an indication upon receiving the power via the direct power circuit, the indication configured to cause verification of the fluid upon the primary system entering a key-on state; and
based at least in part on the indication, causing the direct power circuit to provide the power to a recording system configured to store the difference and the indication to perform a fluid quality check.

10. The method of claim 9, further comprising:
transmitting, based at least in part on the primary system entering the key-off state, an activation command from the low power circuit to the direct power circuit that causes the direct power circuit to provide the power to the fluid level sensor; and
establishing, via a controller area network (CAN), a connection between the low power circuit and the fluid level sensor, wherein the low power circuit receives the first fluid level and the second fluid level via the CAN.

11. The method of claim 9, further comprising:
determining, via the fluid level sensor, a third fluid level within the storage tank at a third time after the first time and before the second time;
determining, with the low power circuit, that an additional difference between the first fluid level and the third fluid level is less than the threshold; and
based at least in part on determining that the additional difference is less than the threshold, preventing the low power circuit from transmitting the command to the tank controller and causing the fluid level sensor to determine the second fluid level at the second time.

12. The method of claim 9, further comprising:
transmitting, based at least in part on the indication, an additional command from the tank controller to a fluid evaluation system upon the primary system entering the key-on state, wherein the additional command causes the fluid evaluation system to determine a fluid concentration associated with the fluid;
receiving, at the tank controller, the fluid concentration; and
determining, based at least on the fluid concentration, that the fluid in the storage tank has been modified.

13. The method of claim 9, wherein the tank controller is further configured to:
transmit, based at least in part on determining that the difference exceeds the threshold, a wake-up signal to the direct power circuit that causes the direct power circuit to provide the power to an additional sensor;
request a storage tank temperature and a storage tank pressure from the additional sensor; and;
cause the recording system to store the storage tank temperature and the storage tank pressure in association with the indication.

14. The method of claim 9, wherein:
the primary system comprises a selective catalytic reduction (SCR) system;
the fluid comprises diesel exhaust fluid (DEF) stored by the storage tank for utilization by the SCR system; and
a fluid composition threshold and a fluid concentration threshold are to be exceed by DEF injected in the SCR system, wherein the fluid quality check includes determining a fluid composition and a fluid concentration prior to the DEF being injected into the SCR system based at least on the difference exceeding the threshold.

15. A system, comprising:
one or more processors; and
a memory storing one or more instructions that are executable by the one or more processors to perform operations comprising:
determining that a circuit switch has transitioned a primary system from a key-on state to a key-off state;
providing, from a power source and via a direct power circuit, power to a fluid level sensor associated with a storage tank, the fluid level sensor determining, upon receiving power from the power source,
a first fluid level of fluid within the storage tank at a first time, and
a second fluid level of the fluid within the storage tank at a second time different from the first time;
determining a difference between the first fluid level and the second fluid level;
determining that the difference exceeds a threshold value; and
based at least in part on determining that the difference exceeds the threshold value, providing, from the power source and via the direct power circuit, power to a recording system operably connected to the one or more processors, the recording system being configured to store an indication that the difference exceeds the threshold value.

16. The system of claim 15, wherein the operations further comprise:
receiving, from the fluid level sensor, a plurality of fluid level measurements captured during a period of time associated with the first time; and
determining, based at least on the plurality of fluid level measurements, a steady state fluid level, wherein the first fluid level is the steady state fluid level.

17. The system of claim 15, wherein the threshold value is a maximum allowable fluid level difference and is indicated by a percentage of the storage tank.

18. The system of claim 15, wherein providing the power to the fluid level sensor further comprises:
transmitting an activation command to the fluid level sensor and the power source;
transmitting a fluid level request to the fluid level sensor;
receiving the first fluid level or the second fluid level; and
transmitting a deactivation command to the fluid level sensor and the power source, wherein the activation command and the deactivation command are transmitted based at least in part on a monitoring schedule.

19. The system of claim 15, wherein the operations further comprise:
- determining that the circuit switch has transitioned the primary system from the key-off state to the key-on state;
- determining, based at least on the indication of the difference, that a fluid quality check is to be performed, wherein the fluid quality check includes causing a fluid evaluation system to determine a fluid concentration associated with the fluid; and
- determining whether the fluid concentration is less than a fluid concentration threshold.

20. The system of claim 19, wherein the operations further comprise:
- transmitting, to an administrator, a recommendation to replenish or replace the fluid in the storage tank based at least in part on determining that the fluid concentration is less than the fluid concentration threshold.

* * * * *